(12) United States Patent
Weiner et al.

(10) Patent No.: US 8,935,100 B2
(45) Date of Patent: Jan. 13, 2015

(54) SYSTEM AND METHOD FOR PRODUCTION RESERVOIR AND WELL MANAGEMENT USING CONTINUOUS CHEMICAL MEASUREMENT

(71) Applicant: NeoTek Energy, Inc., Richardson, TX (US)

(72) Inventors: Douglas B. Weiner, Plano, TX (US); Miroslav Petro, San Jose, CA (US); Dirk De Bruyker, San Jose, CA (US); Marcelo Piotti, Fremont, CA (US)

(73) Assignee: NeoTek Energy, Inc., Richardson, TX (US)

( * ) Notice: Subject to any disclaimer, the term of this patent is extended or adjusted under 35 U.S.C. 154(b) by 0 days.

(21) Appl. No.: 14/106,528

(22) Filed: Dec. 13, 2013

(65) Prior Publication Data

US 2014/0166274 A1 Jun. 19, 2014

Related U.S. Application Data

(60) Provisional application No. 61/738,926, filed on Dec. 18, 2012.

(51) Int. Cl.
*G01N 31/00* (2006.01)
*G01V 3/00* (2006.01)
(Continued)

(52) U.S. Cl.
CPC ................ *E21B 47/00* (2013.01); *G01N 27/12* (2013.01); *G01N 33/2823* (2013.01); *G01N 27/22* (2013.01)
USPC ............................. 702/22; 340/853.1; 367/81

(58) Field of Classification Search
CPC ....... E21B 43/168; E21B 43/12; E21B 43/30; E21B 34/08; E21B 41/0057; E21B 47/10; E21B 47/00; E21B 49/087; E21B 2049/085; G01N 2011/006; G01N 7/00; G01F 1/00; G01F 1/20; G01F 1/74; G05B 23/0243
USPC .......... 702/24, 12, 47, 50, 138, 188; 166/257, 166/263, 266, 250.01, 272.6–272.7; 73/61.47, 152.18, 152.27, 152.31, 73/152.42, 590; 340/855.1, 853.1; 367/81, 367/83; 706/46
See application file for complete search history.

(56) References Cited

U.S. PATENT DOCUMENTS 6,052,520 A    4/2000  Watts, III
7,875,455 B1 *  1/2011  Li et al. ........................... 436/28
(Continued)

OTHER PUBLICATIONS

Notification of Transmittal of the International Search Report and the Written Opinion of the International Searching Authority, or the Declaration dated Apr. 16, 2014 in connection with International Patent Application No. PCT/US2013/075845.
(Continued)

*Primary Examiner* — Toan Le

(57) ABSTRACT

A system performs methods for well and reservoir management for optimized production of fluids in a reservoir. The system includes a knowledge engine configured to receive a plurality of field inputs, process and analyze the field inputs, and provide a plurality of outputs for presentation to an operator. The system also includes a user data interface configured to display the plurality of data outputs. The plurality of field inputs comprises chemical sensing data and at least one of: temperature, pressure, flow rate and concentration of production components from one or more individual wells located within the reservoir, seismic surveys of the reservoir, permeability, geochemistry and lithology of rock formations, and geographic information system (GIS) data associated with the reservoir.

22 Claims, 25 Drawing Sheets

(51) Int. Cl.
*E21B 47/14* (2006.01)
*E21B 47/00* (2012.01)
*G01N 27/12* (2006.01)
*G01N 33/28* (2006.01)
*G01N 27/22* (2006.01)

(56) References Cited

U.S. PATENT DOCUMENTS

| | | |
|---|---|---|
| 2002/0134587 A1 | 9/2002 | Rester et al. |
| 2004/0006436 A1 | 1/2004 | Morgen et al. |
| 2005/0014151 A1 | 1/2005 | Textor et al. |
| 2006/0025897 A1 | 2/2006 | Shostak et al. |
| 2006/0049714 A1 | 3/2006 | Liu et al. |
| 2007/0206440 A1 | 9/2007 | Fripp et al. |
| 2010/0188110 A1 | 7/2010 | Sun |
| 2011/0040501 A1* | 2/2011 | Martin et al. ............ 702/45 |

OTHER PUBLICATIONS

Notification of Transmittal of the International Search Report and the Written Opinion of the International Searching Authority, or the Declaration dated Apr. 18, 2014 in connection with International Patent Application No. PCT/US2013/075852.

* cited by examiner

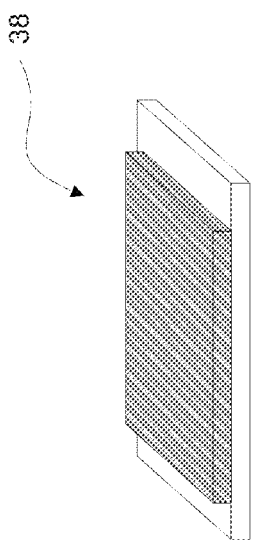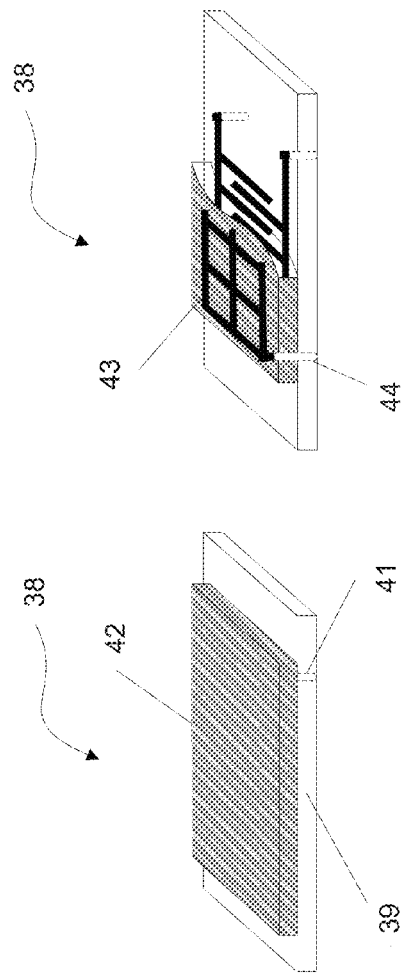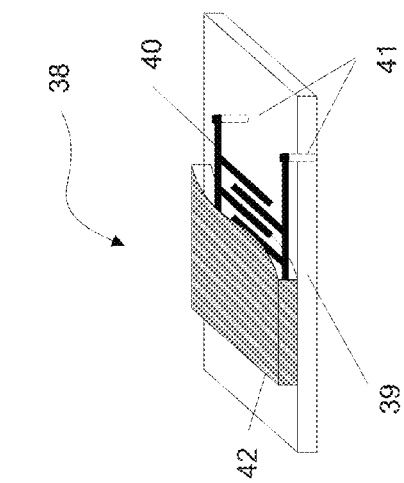

SYSTEM AND METHOD FOR PRODUCTION RESERVOIR AND WELL MANAGEMENT USING CONTINUOUS CHEMICAL MEASUREMENT

CROSS-REFERENCE TO RELATED APPLICATION(S) AND CLAIM OF PRIORITY

The present application claims priority to U.S. Provisional Patent Application Ser. No. 61/738,926 filed Dec. 18, 2012, entitled "PRODUCTION RESERVOIR AND WELL MANAGEMENT SYSTEM USING CONTINUOUS CHEMICAL MEASUREMENT". The content of the above-identified patent document is incorporated herein by reference. The present application also includes some common text and/or figures as, but is otherwise unrelated to, concurrently filed U.S. patent application Ser. No. 14/105,389, which is hereby incorporated by reference.

TECHNICAL FIELD

The present disclosure relates to direct chemical detection in a complex single-phase or multiphase flow from a well or in a pipeline. The present disclosure also relates to real-time chemical sensing utilizing temporary or permanent apparatuses, such as logging tools, with electronics for measuring the chemical properties of a single-phase or multiphase flow in one or more wells. The present disclosure further relates to a real-time chemical sensor network system and method to gather chemical flow data, both subterranean and at the surface. In addition, the present disclosure relates to the management of underground reservoirs, such as oil, natural gas, water and geothermal reservoirs, for production optimization.

BACKGROUND

Oil, natural gas, water, or other wells can be likened to sophisticated high pressure, high temperature factories. Well and reservoir management often requires a system-level approach with direct knowledge of the processes and their outcomes for the most effectively optimized production. Geochemical modeling capabilities are fairly advanced, but applications to field problems remain challenging due to limited availability of relevant and timely field data and the scale dependence of parameters. Current approaches often only allow snapshots of the outcomes and, not being continuous, can only guess at the processes. This causes inefficient remediation efforts that are sometimes even destructive.

SUMMARY

In some embodiments, the present disclosure provides a continuous method and system for reservoir and well management based on direct in-well chemical measurements for a reservoir fluid composed of liquid, gas or supercritical fluid components with dissolved or dispersed solids, coupled with pre-production or other production data on the reservoir. By continuous processing of chemical data delivered from remote sites, some embodiments of the present disclosure can identify and respond quickly when wells go offline or move outside normal operating conditions. This can have huge benefits in preventing hazardous outcomes, improving safety and environmental management, and progressively reduce uncertainty, which can ultimately lead to reduced operating costs.

Various advantages can be obtained depending on the implementation. For example, some embodiments of the present disclosure reduce uncertainty in a broad sense to allow production extension through optimum reservoir management. Some embodiments of the present disclosure also provide for more cost effective monitoring and production of a well or reservoir. Some embodiments of the present disclosure further decrease the time it takes to obtain a real-time dynamic fluid flow full-field multiphase reservoir simulation model that fits obtained data and that can be used for timely interpretation of the simulation model for prediction of future situations. Moreover, some embodiments of the present disclosure provide a direct chemical measurement system for surface or sub-surface deployment that can be used in the harsh environment of a well. In addition, some embodiments of the present disclosure provide a chemical sensor whose data processing for classification, identification and concentration is completely self-contained so that its external communication requirements for data transportation are reduced or minimized.

In particular embodiments, the technologies described here and the information they provide can be integrated with standard reservoir and production management tools, databases and models to contribute information to guide real-time reservoir optimization models.

In one embodiment, a system for well and reservoir management for optimized production of fluids in a reservoir is provided. The system includes a knowledge engine configured to receive a plurality of field inputs, process and analyze the field inputs, and provide a plurality of outputs for presentation to an operator. The system also includes a user data interface configured to display the plurality of data outputs. The plurality of field inputs comprises chemical sensing data and at least one of: temperature, pressure, flow rate and concentration of production components from one or more individual wells located within the reservoir, seismic surveys of the reservoir, permeability, geochemistry and lithology of rock formations, and geographic information system (GIS) data associated with the reservoir.

In another embodiment, a method for well and reservoir management for optimized production of fluids in a reservoir is provided. The method includes receiving, at a knowledge engine, a plurality of field inputs; processing and analyzing, at the knowledge engine, the field inputs; providing, at the knowledge engine, a plurality of outputs for presentation to an operator; and displaying, at a user data interface, the plurality of data outputs. The plurality of field inputs comprises chemical sensing data and at least one of: temperature, pressure, flow rate and concentration of production components from one or more individual wells located within the reservoir, seismic surveys of the reservoir, permeability, geochemistry and lithology of rock formations, and geographic information system (GIS) data associated with the reservoir. The plurality of data outputs may include processed chemical sensing data from one or more individual wells located within the reservoir and at least one of: chemical flows between wells, prescriptive remedies for individual well problems or reservoir problems, and various user defined and configurable alert events.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which like reference numerals represent like parts:

FIGS. 8A-8D illustrate example chemical sensor transducers in accordance with this disclosure;

DETAILED DESCRIPTION OF THE INVENTION

Figure 1:
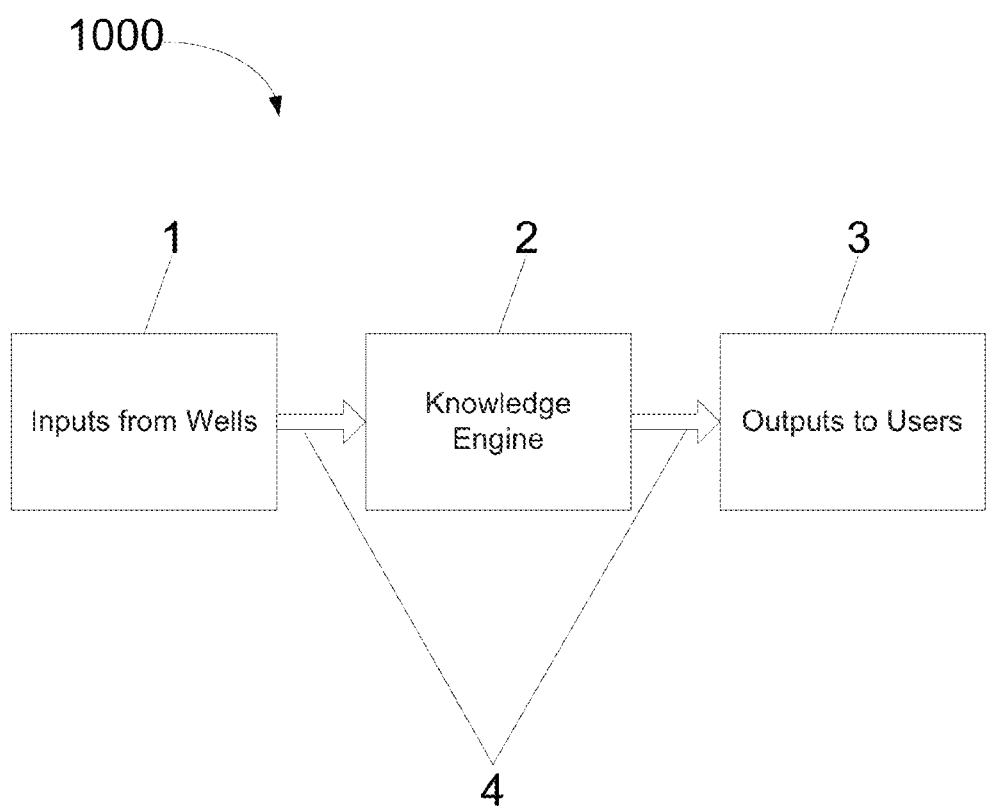
FIG. 1 illustrates an example Production Reservoir Management System based on direct chemical measurements in accordance with this disclosure.

FIGS. 1 through 26B, described below, and the various embodiments used to describe the principles of the present disclosure in this patent document are by way of illustration only and should not be construed in any way to limit the scope of this disclosure. Those skilled in the art will understand that the principles of the present disclosure may be implemented in any type of suitably arranged device or system.

The following documents are hereby incorporated into the present disclosure as if fully set forth herein:

U.S. PATENT DOCUMENTS

U.S. Pat. No. 4,969,130 to Wason et al. entitled "System for Monitoring the Changes in Fluid Content of a Petroleum Reservoir;"

U.S. Pat. No. 7,478,024 to Gurpinar et al. entitled "Integrated Reservoir Optimization;"

U.S. Pat. No. 5,680,899 to Waid et al. entitled "Electronic Wellhead Apparatus for measuring properties of Multiphase Flow;"

U.S. Pat. No. 3,995,488 to Crawley entitled "Dielectric Change Sensing Device;"

U.S. Pat. No. 5,055,784 to Jaeger et al. entitled "Bridgeless System for Directly Measuring Complex Impedance of an Eddy Current Probe;"

U.S. Pat. No. 5,514,337 to Groger et al. entitled "Chemical Sensor Using Current or Resonant Electromagnetic Circuit Detection;"

U.S. Pat. No. 5,227,342 to Anderson et al. entitled "Process of Making Porous Ceramic Materials with Controlled Porosity;"

U.S. Pat. No. 6,370,965 to Knapp entitled "Capacitive Sensing Array Devices;" and U.S. Pat. No. 8,165,986 to Niu et al. entitled "Method and System for Real Time Production Management and Reservoir Characterization."

ADDITIONAL REFERENCES

Smith et al., "The Road Ahead to Real-Time Oil & Gas Reservoir Management," Transactions of the Institution of Chemical Engineers: Chemical Engineering Research and Design, Vol. 76A, pp. 539-552, 1998;

Mukhopadhyay, "Novel Planar Electromagnetic Sensors: Modeling and Performance Evaluation," Sensors 2005, 5, pp. 546-579;

Konishi, "Microwave Integrated Circuits," CRC Press, 1991 ISBN 0-8247-8199-6;

Shida, "A New Multifunctional Sensor for Measuring the Concentration and Temperature of Dielectric Solution," SICE 2002, Proceedings of the 41st SICE Annual Conference, 5-7 Aug. 2002, page 575;

Bakar et al., "New Contactless Eddy Current Sensor for the Measurement of Concentration of Electrolyte Solution," SICE '97, Proceedings of the 36th SICE Annual Conference, International Session Papers, pp. 937-940, 29-31 Jul. 1997, doi: 10.1109/SICE.1997.624882;

Pallas-Areny et al., "Sensor and Signal Conditioning," 2nd ed. NY, USA: John Wiley & Sons, 2001;

Bhat, "Salinity (Conductivity) Sensor Based on Parallel Plate Capacitors," Graduate School Theses and Dissertations, University of South Florida, paper 2784, 2005;

Tulliani et al., "Porous Alumina and Zirconia Bodies Obtained by a Novel Gel Casting Process," Advances in Bioceramics and Porous Ceramics: Ceramic Engineering and Science Proceedings, Volume 29, Issue 7, John Wiley & Sons, 2009;

Igreja et al., "Dielectric Response of Interdigital Chemocapacitors: The Role of the Sensitive Layer Thickness," Sensors and Actuators B: Chemical, Vol. 115 (1), May 23, 2006; and Staginus et al., "Surface-Engineered Sensors: Polymer-based Sensors for the Capacitive Detection of Organic Pollutants in Water," Proceedings of IMCS 2012—The 14th International Meeting on Chemical Sensors, pp. 1141-1144.

For years, oil and gas company operators have been trying to integrate data, interpretations, models, simulations, and effects of development and production decisions in such a way as to optimally deplete a reservoir according to a business model and economic constraints. Oil and gas wells can be likened to high pressure, high temperature tubular reactors whose geometry and sophistication is complex. As stated by Smith and Geoffrey in "The Road Ahead to Real-Time Oil & Gas Reservoir Management," a reservoir "can be viewed as an underground factory whose overall efficiency in producing saleable products is determined by the way that its individual production units are deployed and coupled in the light of market needs." Chemicals and chemical processes are the chief factor affecting well and reservoir operation and sustainability. The simultaneous flow of oil, gas and water in porous media affects practically every aspect of the reservoir engineer's job of optimizing the recovery from a well and from a reservoir.

Optimized reservoir management and operation typically involves a determination of which formations are producing, which fractures are flowing, what is specifically flowing and what the individual flow rates are. Seismic exploration reveals regional geology that indicates geometry, internal architecture, rock properties and their variability, as well as hinting at potential mechanical processes that will be triggered as the well is produced. Logging can also reveal porosity and permeability for each lithologic environment found within each well. Coring provides general trends, identifying the azimuth of a fracture plane. Pressure is another commonly used metric, but even very low-permeability sites show that pressure varies widely within the same wellbore, thus reservoir pressure is generally not well known. A "good" reservoir may deteriorate as a consequence of fluid circulation because injected fluids may self-enhance short-circuiting pathways and because the solvent properties of water and other fluids used at injection wells to improve production can induce mineral dissolution and precipitation at geothermal temperatures.

Various approaches have been taken in the oil and gas industry to combat these issues. For example, hybrid self-learning reservoir models have been developed and utilized when data is scarce, which is often the case in early reservoir development. These models balance accuracy of data fitting with predictive ability by appropriate selection of model algorithms. Reservoir models may employ a first-principles structure along with empirical constitutive related equations (such as Darcy's law, ideal gas law, and pressure-drop relationships) to the chemical processes that are actually occurring. They often rely on incoming data to identify and regularly update values of many of the algorithms' parameters as they try to estimate the actual situation in a reservoir.

In systems with hundreds of wells, first-principles models may fall apart because there is not enough processing power to calculate solutions. There is an overwhelming amount of data used to make reasonable inferences, either directly or through comparison, since direct measurement of the actual processes and their results downhole are not available. Simpler solutions yield results that decisions can be based on; although there is great potential for error, the results usually provide reasonable solutions at that specific moment. In practice, engineers and operators have sophisticated models available but still make most of their subjective decisions based on simple EXCEL spreadsheets because there is not enough time to run the complex models before making a decision.

Chemical sensing has played a part in the development of wells and reservoirs during production, but it is limited in nature due to inaccuracies and timeliness. During production, fluid samples are occasionally analyzed at an offsite laboratory to determine their chemical content and help determine the production capability of the well. As these samples are removed from the individual wells, the temperature and pressure of the samples change from what is found downhole or even at the wellhead. This changes the composition as (i) the bubble point is reached at lower pressures causing out-gassing, (ii) various chemicals co-precipitate at lower temperatures as they come out of saturation and (iii) are often chemically recombined to create new compounds that were non-existent under the original conditions in the well.

Methods in current use involve measuring indirect properties of these chemicals or occasionally measuring them directly on a sampled basis with long times between samples. This information is then compared with models, which are continuously revamped to match the current data. If a reservoir simulation model is not frequently updated with new data and new history matches conducted, the "optimized" solutions rapidly become irrelevant and may then be put aside to return to traditional tried and tested decline-curve and water-cut analysis. Those analyses provide the reservoir managers with an understanding of what is actually happening in active wells but offer little in terms of optimization solutions.

Continuously-monitored chemical-based sensors could reveal changes in the production quality and quantity in relation to changes in underground fluid flow and geological structure not visible to seismic and other sensors with various chemicals present in the reservoir moving along the flow-paths. These chemicals serve as tracers to reveal when and where water intrusion is happening, identify the start of channeling, visualize distribution of the flood to determine how well an injection sweep is performing, or even detect precursors to corrosion such as caused by hydrogen sulfide and naphthenic acids or the formation of waxes and asphaltenes well before any restriction to a production flow happens.

In enhanced oil recovery (EOR), chemical disequilibrium between injected fluid and the reservoir lithology is a major issue. To maintain production rates, rock/fluid interactions are monitored for scale production in the reservoir that reduces permeability or for the creation of preferred pathways reducing extraction efficiency. Monitoring a breakthrough of the EOR agent such as carbon dioxide from an injection to production wells is critical for achieving better sweep efficiencies and subsequently higher production flows and overall reservoir depletion rate.

There is a need to provide a more accurate, efficient and effective process for the managing of wells and reservoirs. Providing real-time continuous predictive chemical analytics allow well interventions to be managed proactively ahead of serious well or reservoir damage. Current tools do not provide this and are based on algorithmically connecting "guesstimates" obtained through indirect measurements. There is also a need to continuously capture direct measurements of these chemicals with a sensor that can be used in real-time for a wide range of chemicals and that reacts quickly to changes, while still being able to sense a wide range of chemical concentrations in three phase flows.

Reference is now made in detail to various embodiments of this disclosure, examples of which are illustrated in the figures. Each example is provided by way of explanation and is not meant as a limitation. For example, features illustrated or described as part of one embodiment can be used on or in conjunction with other embodiments to yield yet further embodiments. It is intended that the present disclosure include such modifications and variations. Although specific features of various embodiments of the disclosure may be shown in some drawings and not in others, this is for convenience only. In accordance with the principles of the disclosure, any feature of a drawing may be referenced and/or claimed in combination with any feature of any other drawing.

As used here, the term "microcontroller" is not limited to integrated circuits referred to in the art as a computer but broadly refers to a controller, microprocessor, microcomputer, programmable logic controller (PLC), digital signal processor (DSP), application specific integrated circuit, and other programmable circuits, and these terms are used interchangeably herein. It should be understood that a processor and/or a control system can also include memory, input channels, and/or output channels and peripherals. Peripherals may include, without limitation, analog to digital converters (ADCs), digital to analog converters (DACs), pulse width modulators (PWMs), universal serial bus (USB) interfaces, and RS-232 transceivers. Memories may include, without limitation, computer-readable volatile media such as a random access memory (RAM) and computer-readable non-volatile media such as flash memory.

Processors described herein process information transmitted from a plurality of electrical and electronic devices that may include, without limitation, sensors, actuators, compressors, control systems, and/or monitoring devices. Such processors may be physically located in, for example, a control system, a sensor, a monitoring device, a desktop computer, a laptop computer, and/or a programmable logic controller (PLC). RAM and other storage devices store and transfer information and instructions to be executed by the processor(s). RAM and other storage devices can also be used to store and provide temporary variables, static (i.e., non-changing) information and instructions, or other intermediate information to the processors during execution of instructions by the processor(s). Instructions that are executed may include, without limitation, system control commands, data parsing and mathematical algorithms. The execution of sequences of instructions is not limited to any specific combination of hardware circuitry and software instructions.

Some embodiments of a Production Reservoir Management System (PRMS) of the present disclosure include or support a process involving continuous or near-continuous chemical monitoring of one or more wells in a reservoir, an apparatus to provide the continuous or near-continuous monitoring, analysis of the measured data, and output and storage of the analysis results. Some embodiments of the present disclosure also utilize chemical sensors resident in various well flows (at the surface or sub-surface) and utilize a communication network to communicate data to a central location. Well flows are a multi-component mixture with the components having a specific set of chemical and physical attributes (such as phases) and each component having additional characteristics relative to other components (such as concentrations) or in time (such as flow rates) or space (such as positioning along the wellbore).

Production Reservoir Management System

FIG. 1 illustrates an example Production Reservoir Management System (PRMS) 1000 based on direct chemical measurements in accordance with this disclosure. The embodiment of the PRMS 1000 shown in FIG. 1 is for illustration only. Other embodiments of the PRMS 1000 may be used without departing from the scope of this disclosure.

The PRMS 1000 of FIG. 1 includes inputs 1, a knowledge engine 2, outputs 3, and communications 4. The inputs 1 can relate to one or more individual wells or to an entire reservoir. The knowledge engine 2 processes the inputs 1 and derives actionable information. The outputs 3 are made available to users, such as via display devices, as parameters to reservoir models or searchable databases, or in other ways. The communications 4 provide data transport between various locations.

Figure 2:
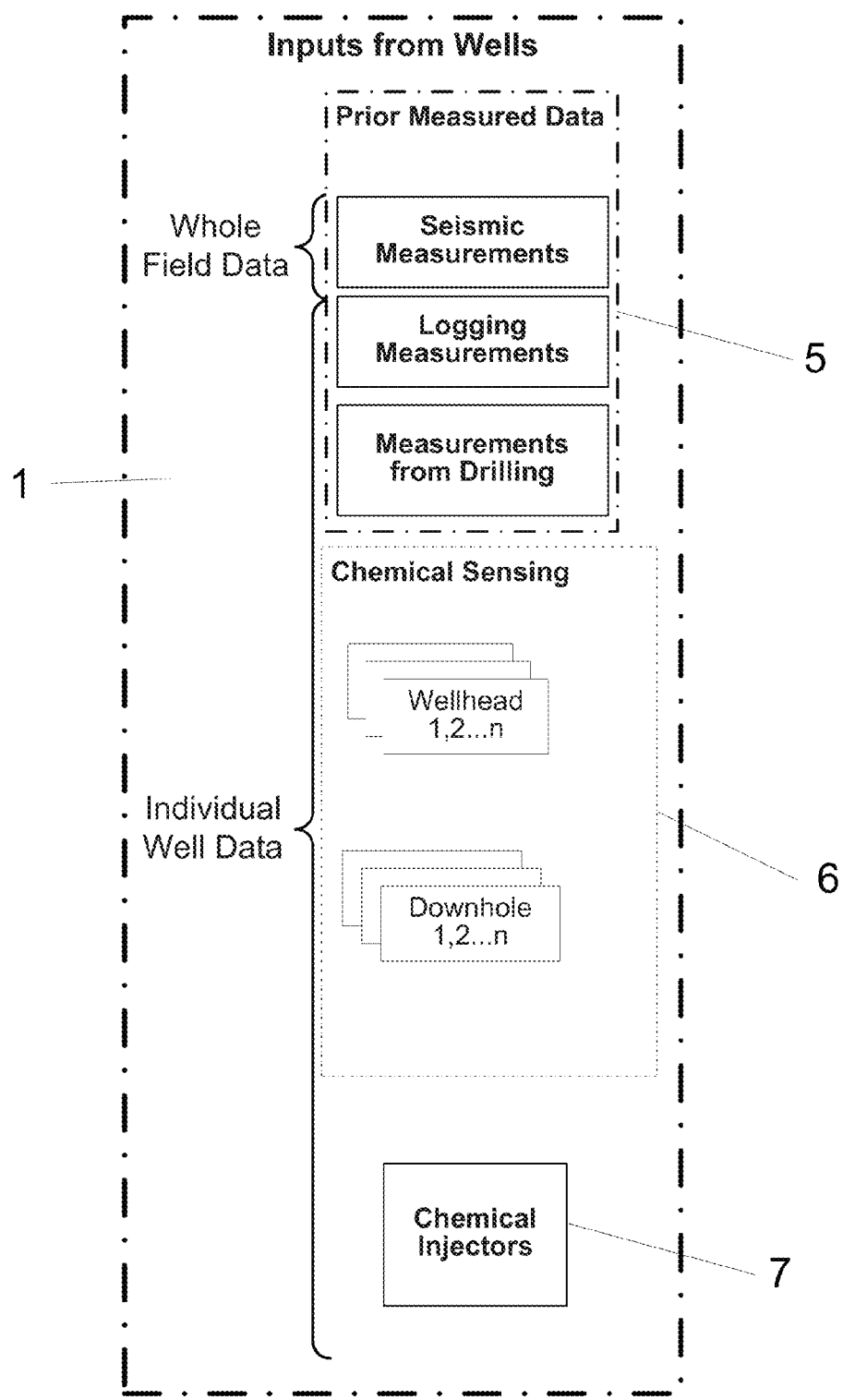
FIG. 2 illustrates example inputs to the Production Reservoir Management System in accordance with this disclosure.

FIG. 2 illustrates example inputs 1 to the Production Reservoir Management System 1000 in accordance with this disclosure. The embodiment of the inputs 1 shown in FIG. 2 is for illustration only. Other embodiments of the inputs 1 may be used without departing from the scope of this disclosure.

Inputs that are snapshots of specific points in time and have been measured external to the system are called "prior measured data" 5. This data can be obtained for either the entire reservoir or on an individual well basis. The data 5 can include data obtained from seismic surveys, data taken while drilling, and logging measurements from various common tools that provide information on temperature, pressure, porosity, flow rate, water cut, and other common parameters. The PRMS 1000 can utilize available additional data to further optimize and extend its outputs. Continuous chemical sensing data 6, taken at the surface or sub-surface or both by apparatuses disclosed herein, provides chemical presence indication and concentration data for a single-phase or multiphase flow, such as is found in an oil, gas, water or geothermal well. The PRMS 1000 can also utilize current process data 7, such as what chemicals are utilized and their concentration for injector wells located in the reservoir. Additionally, this data can include the geo-location of the injector wells.

Figure 3:
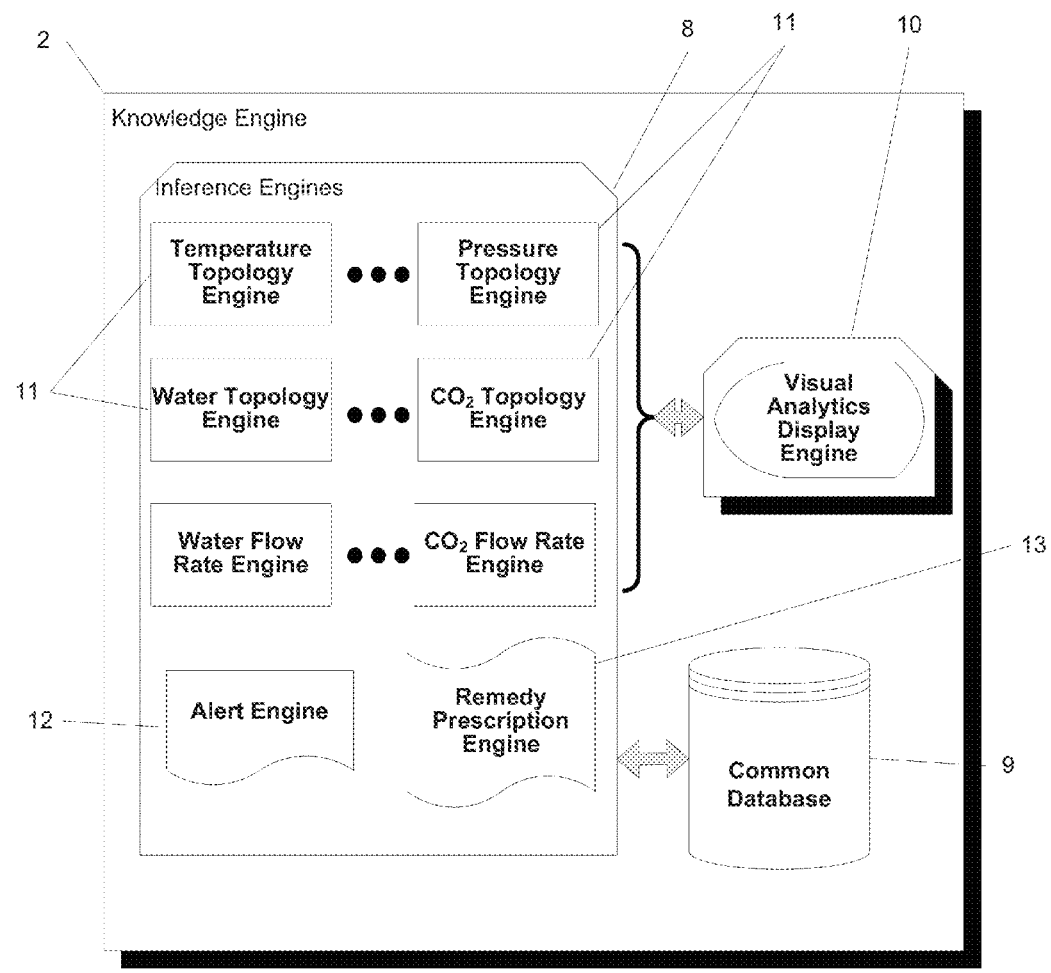
FIG. 3 illustrates an example Knowledge Engine in the Production Reservoir Management System in accordance with this disclosure.

FIG. 3 illustrates an example of the Knowledge Engine (KE) 2 in the Production Reservoir Management System 1000 in accordance with this disclosure. The embodiment of the KE 2 shown in FIG. 3 is for illustration only. Other embodiments of the KE 2 may be used without departing from the scope of this disclosure.

The KE 2 supports the operational rule set to provide reservoir operational optimization. The KE 2 includes a set of inference engines 8, a common database 9, and a visual analytic display engine 10. The common database 9 is an incoming storage repository for prior measured data, continuously obtained chemical sensing data 6, and current process data 7. It also is a repository for output results generated by the inference engine set 8. The inference engine set 8 includes an engine 11 for each specific chemical or characteristic of interest that is being sensed. The inference engine set 8 also includes alert engines 12 that can use a default set of rules based on standard industry practice (such as operational pressure and the formation of waxes) or user-defined rules (such as related to the breakthrough of $CO_2$ on a single well or multiple wells during an injection sweep). A remedy prescription engine 13 can be used to identify solutions to various problems that can be encountered.

Chemical measurements are fused with other co-existing or prior measured data 5 in the topology engines 11, whose output is combined with geographic information system (GIS) data in the visual analytic display engine 10 to allow the determination of flow patterns and chemical contour mapping over time. This allows the reservoir to be viewed on an actual dynamic basis. The molecular characteristics of the individual chemical components produced, along with the identification of subterranean rock formation boundaries and formation porosity (which can be determined from the prior measured data 5), allows for the topographical mapping of multi-component chemical flows.

Figure 4:
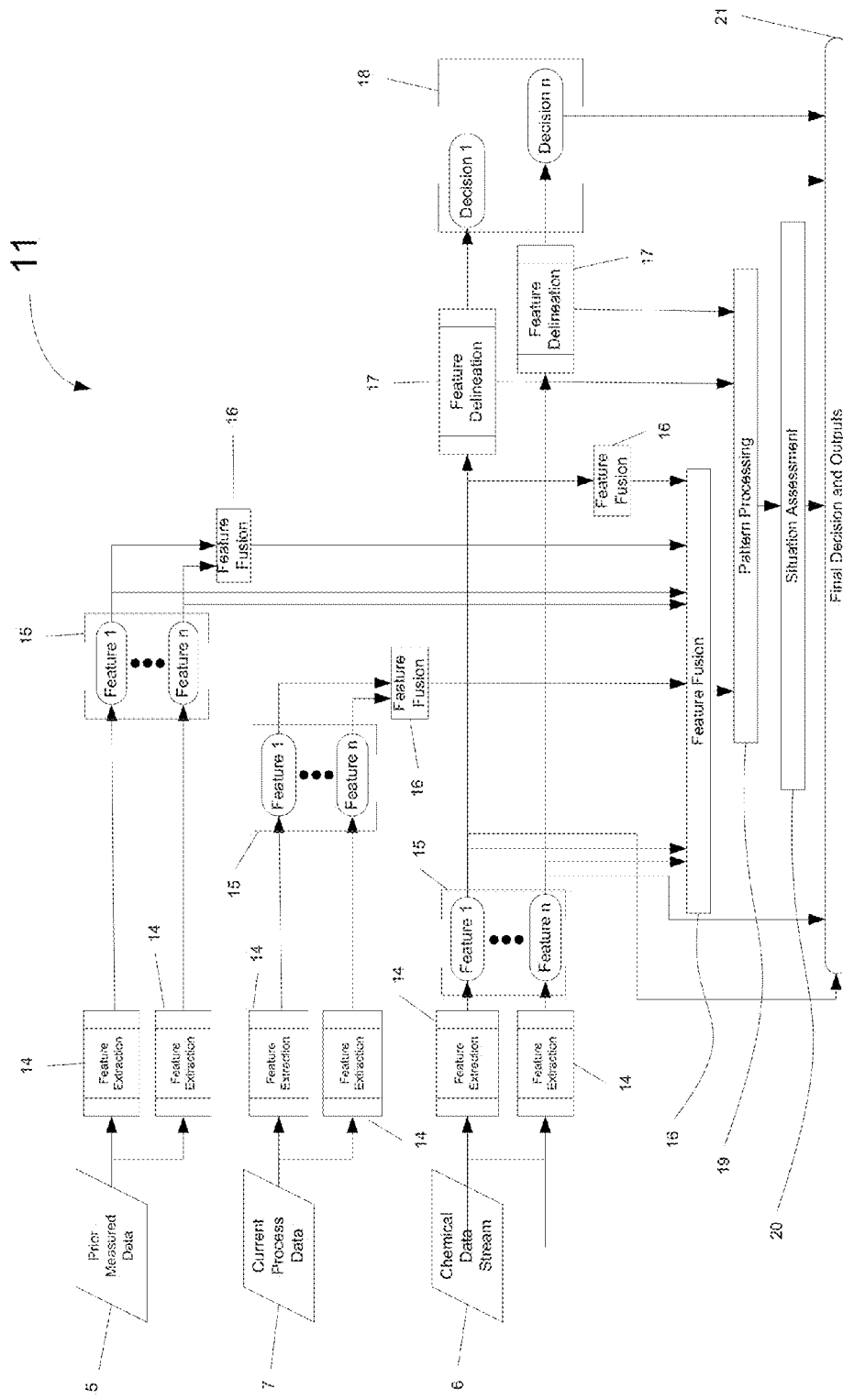
FIG. 4 illustrates an example generalized topology engine within the Knowledge Engine in accordance with this disclosure.

FIG. 4 illustrates an example generalized topology engine 11 for use within the Knowledge Engine 2 in accordance with this disclosure. The embodiment of the engine 11 shown in FIG. 4 is for illustration only. Other embodiments of the engine 11 may be used without departing from the scope of this disclosure.

The engine 11 performs various mathematical operations, in whole or in part and individually or in combination, using the prior measured data 5, continuous chemical sensing data 6 and/or the current process stream 7. These operations may include, but are not limited to, feature extraction operations 14 resulting in output feature sets 15, feature fusion operations 16, feature delineation operations 17 resulting in decision sets 18, and pattern processing 19 including pattern matching used in a situation assessment 20. The desired features that have been extracted, along with those that have been obtained from the mathematical operations and the situation assessment, are used to develop a final decision as to the current state and possible actions to be taken pertinent to the specific function of the engine. These decisions and actions become outputs 21 of the engine 11 for use by the visual analytics display engine 10, storage in the common database 9, input to reservoir models, or display to the user.

Figure 5:
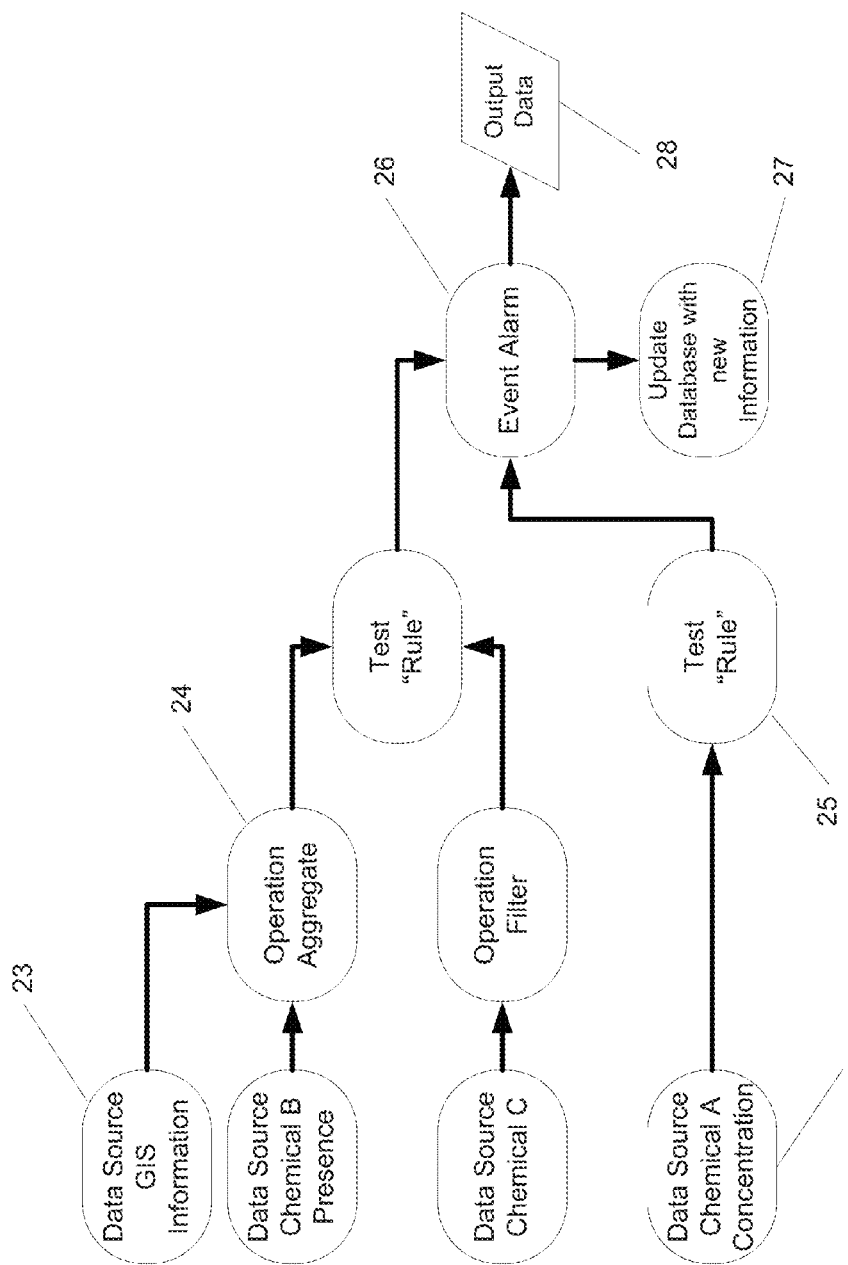
FIG. 5 illustrates an example rule for an alert engine within the Knowledge Engine in accordance with this disclosure.

FIG. 5 illustrates an example rule for an alert engine 12 within the Knowledge Engine 2 in accordance with this disclosure. The embodiment of the rule shown in FIG. 5 is for illustration only. Other embodiments of the rule may be used without departing from the scope of this disclosure.

Inputs 22 for specific chemical measurements, such as presence, concentration and flow rate, are combined with external data 23 through mathematical algorithmic operations 24. The operations are performed on individual input data elements/streams or combinations of input data elements/streams as required by the specific information to be obtained. Outputs from the mathematical operations 24 are fed to an appropriate test rule 25, of which there can be a single rule or multiple rules applying to a specific data element/stream or set of data elements/streams and the appropriate mathematical operations. The output results of the test rule 25 can trigger an alert event 26, an update of the database event 27, and the output of data to a user.

Figure 6:
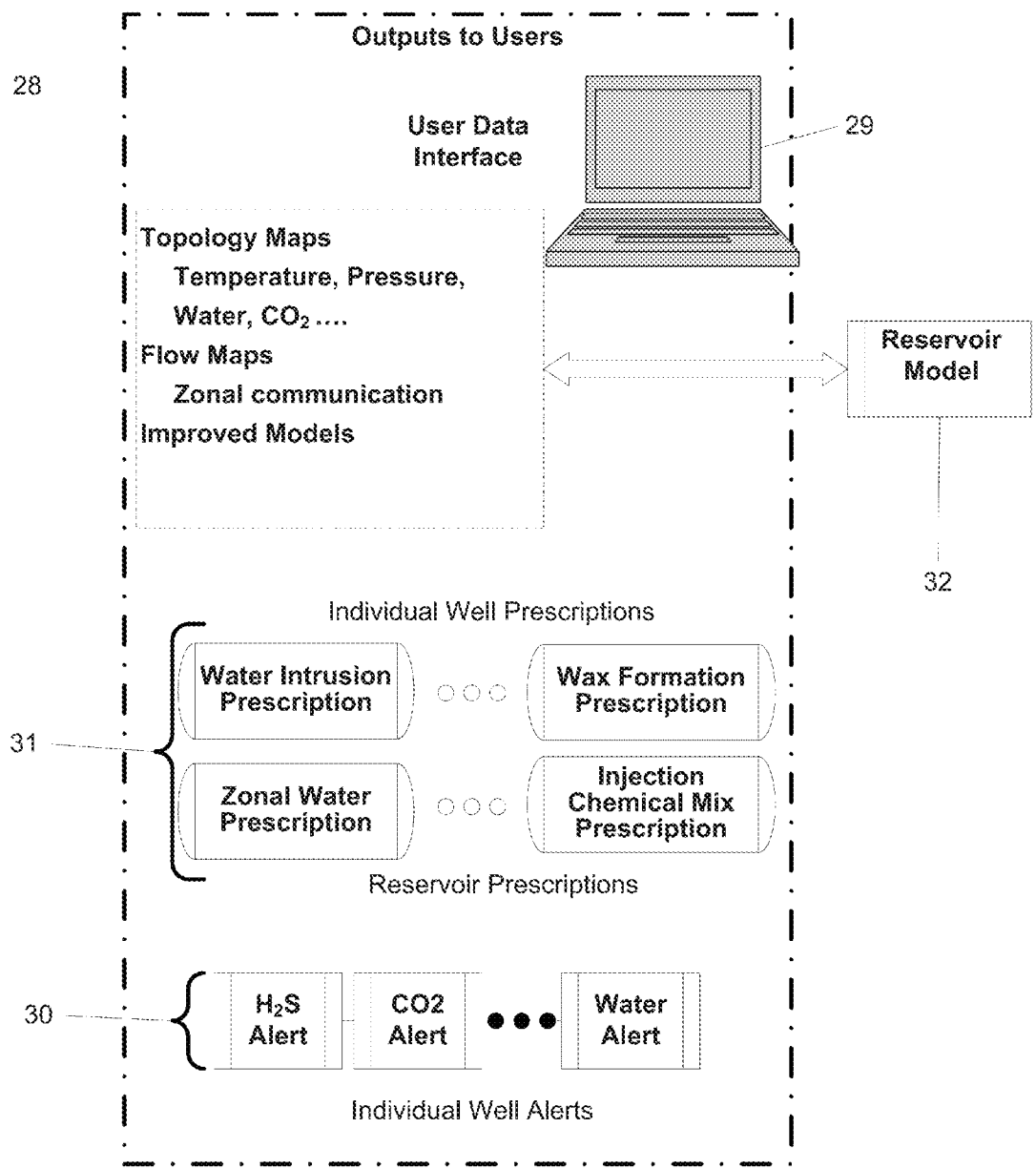
FIG. 6 illustrates example outputs of the Production Reservoir Management System in accordance with this disclosure.

FIG. 6 illustrates example outputs 28 of the Production Reservoir Management System 1000 in accordance with this disclosure. The embodiment of the outputs 28 shown in FIG. 6 is for illustration only. Other embodiments of the outputs 28 may be used without departing from the scope of this disclosure. In some embodiments, the outputs 28 may represent the outputs 3 of FIG. 1.

The outputs 28 provide for reservoir production optimization through presentation of reduced and analyzed data from the knowledge engine 2. Visualization of data occurs on a User Data Interface (UDI) 29, which can be implemented on a data terminal, personal computer (PC), or handheld mobile device. The dynamic monitoring of individual wells and topological breakthrough times and patterns in the reservoir can also be monitored. Optimized reservoir management occurs due to specific knowledge of where problems are occurring in a well as defined by individual system and user defined alerts 30. This provides better remediation techniques via prescriptive remedies 31 tailored to the problem occurring, which can take into consideration the remedy's effect on the local set of wells as well as the entire reservoir. As an example, water intrusion can be detected by the present disclosure at an early stage prior to causing significant damage to an oil or gas well, allowing a simple prescriptive remedy of decreasing pressure. However, if the production rate is desired to be kept constant (so the pressure cannot be decreased), the effect can also be monitored more globally to see possible changes to reservoir dynamics related to this issue.

Continuous chemical measurements of the chemical factory of a reservoir and dynamic topographical mapping of reservoir flows on a chemical basis or class of chemical bases can be used to improve a reservoir model 32. This allows better determination of where infield drilling is most productive from an overall reservoir standpoint, allowing the possibility of fewer infield wells drilled. The model structure for interaction with the PRMS 1000 can support a self-learning adaptive scheme that optimizes multiphase fluid migration in reservoirs while integrating wellhead restrictions and business constraints and continuously optimizing reservoir performance while satisfying surface and sub-surface constraints.

Figure 7:
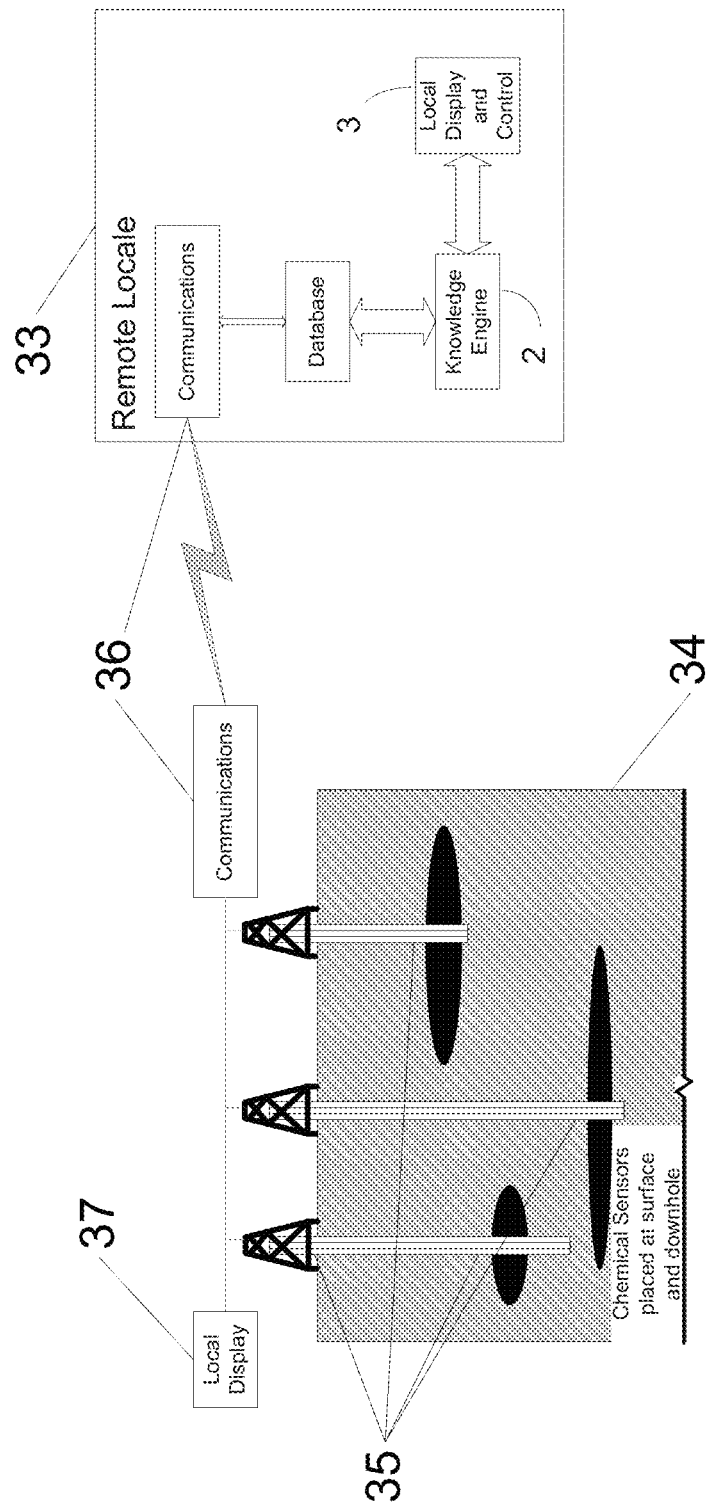
FIG. 7 illustrates an example use where the Production Reservoir Management System's knowledge engine and outputs are remote from a reservoir in accordance with this disclosure.

FIG. 7 illustrates an example use where the knowledge engine 2 and outputs 3 of the Production Reservoir Management System 1000 are remote from a reservoir in accordance with this disclosure. The embodiment of the shown in FIG. 7 is for illustration only. Other embodiments may be used without departing from the scope of this disclosure.

Here, the knowledge engine 2 and outputs 3 are at a remote locale 33 from a reservoir 34 and chemical sensors 35. A communication network 36 allows the monitoring of a producing reservoir by production engineers at an off-site location as well as data aggregation within a field. This allows the production engineer to easily monitor multiple reservoirs using real-time alerts of the present disclosure whose rules are defined by the reservoir engineer to quickly react to problems that impact production and would otherwise be unnoticed for days. Additionally, information that is monitored but pertinent to local immediate well operations derived by the knowledge engine 2 is available locally via a local display 37, which can be tied into the communication network 36.

Chemical Sensors

Being able to detect chemicals in a well flow may require sensors that are selectively sensitive to individual chemical components and can withstand the harsh environment of a well with its high temperature, high pressure, and (for some wells) abrasive nature of the flow. There have been many commercial chemical sensors developed on the principle of interaction of a chemically-sensitive material with an electromagnetic signal, such as eddy current induction or resistance-inductance-capacitance (RLC) circuits. However, current sensors typically do not stand up to the environmental conditions found downhole, especially the abrasiveness of the flow, making them useless for permanent installations. Additionally, current sensors typically are not sufficiently differentiating and accurate to provide a true chemical analysis including an indication of abundance.

Eddy current systems date back to the 1920s with the advent of the grid dip meter. They are usually used to provide a non-contact probe that measures a material property in a non-destructive manner. The probe is a separate component from the material, which is usually part of another component.

The present disclosure provides chemical sensors that use a combination of mechanical structures, sensing material selectivity for specific chemicals or class of chemicals, and sensor dynamic range geometry and measurement technique. The present disclosure also includes a mechanical configuration that makes it useful in harsh environments.

FIGS. 8A-8D illustrate example chemical sensor transducers in accordance with this disclosure. The embodiments of the transducers 38 shown in FIGS. 8A-8D are for illustration only. Other embodiments of the transducers 38 may be used without departing from the scope of this disclosure.

FIG. 8A shows a mechanical depiction of a chemical sensor transducer 38. FIG. 8B shows the constituent parts of the transducer 38, including an induction and reader platform 39, field electrodes 40, plated through vias 41, and a chemically-sensitive and selective sensing material 42. This mechanical format lends itself to harsh environments as the structure forms a "sandwich" that exposes only the sensing material and the platform to the harsh environment but not the printed circuitry or any electronics. This can be seen in FIG. 8C where the sensing material 42 fully covers and encapsulates the field electrodes 40 and the plated through vias 41.

An alternate embodiment of the transducer 38 is shown in FIG. 8D, which adds a conductive grid 43 on top of the sensing material 42 with additional secondary plated through vias 44 for connection to the backside of the platform 39. The grid 43 can be charged positively or negatively to provide additional chemical selectivity based on the ionic charge of the molecules in the analyte stream. The grid 43 can also be used to effectively turn off a sensor whose natural ionic charge affinity can be negated by an opposite charge on the grid.

Figure 9A:
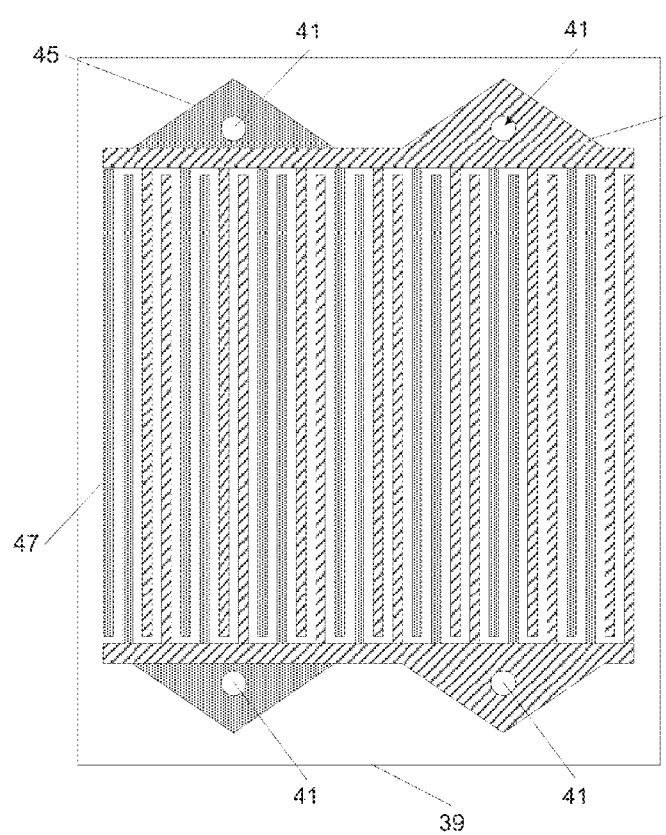
FIGS. 9A-9C illustrate example chemical sensor transducer electrodes in accordance with this disclosure.
Figure 9B:
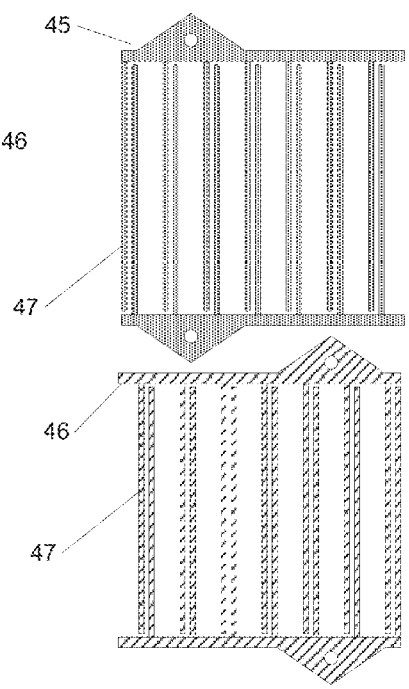
Figure 9C:
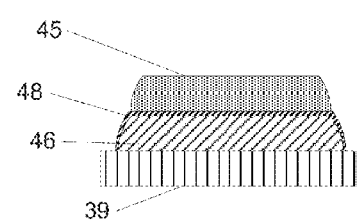

FIGS. 9A-9C illustrate example chemical sensor transducer electrodes 45-46 in accordance with this disclosure. The embodiments of the electrodes 45-46 shown in FIGS. 9A-9C are for illustration only. Other embodiments of the electrodes 45-46 may be used without departing from the scope of this disclosure.

Each electrode 45-46 includes two sets of interdigital fingers 47 and is coupled to plated through vias 41. This example shows two electrodes 45-46, although more electrodes could also be used. This structure allows selective driving of the various interdigital fingers 47 to provide variation in penetration of an electromagnetic field, from wholly-contained within the transducer sensing material 42 to beyond the sensing material 42 and into the analyte, with the same total applied electromotive force applied at the electrodes.

FIG. 9B shows details of the mechanical structure of the electrodes 45-46, each with two separate sets of fingers 47. FIG. 9C shows the vertical structure of the electrodes, where a dielectric insulator 48 is placed between the metallization layers forming the electrodes 45-46 at the points where they would overlap. The fingers 47 of both sets are co-planer. This structure may be extended to a larger number of electrodes to form additional driving points. When both sets of fingers 47 are driven, this results in a more tightly coupled electrode structure, and the electric field may not penetrate outside of the sensing material 42 shown in FIGS. 8B and 8C. If only one set of fingers 47 is driven, a looser electrically coupled structure is created, and the field can penetrate farther outside the sensing material 42. The electrode structure density used (finger spacing) relates to the thickness of the sensing material to be used with (deposited on) the electrode. The use of interlaced fingers 47 is just one technique for forming the electrode. Other techniques could also be used, such as concentric rings.

To withstand harsh environments, in some embodiments the induction and reader platform 39 can be made of a single crystal form of $AL_2O_3$ or similar ceramic material. This material is insulative, abrasion resistant, and can withstand high pressure. It also has a low coefficient of thermal expansion but is readily processed using standard industry processes found in the manufacture of printed circuit boards.

The chemical sensing material 42 can have a multi-component make up. A base material can be formed from a material that is neutral or mostly neutral from a chemical selectivity standpoint. In many cases, it is composed of a cross-linked backbone of inorganic and organic polymers. The backbone material structure can be derivatized for chemical sensitivity and selectivity in order to obtain its final functional form. The resulting sensing material's permeability, chemical polarity, and dielectric properties are selectable and controllable by choice of both the backbone precursors and functional groups. The base material's hardness can provide abrasion resistance, and its compressible strength can provide the ability to withstand pressure. Both may be needed for long term operation downhole.

In the present disclosure, the property of controlled nano-porosity can be used to influence sensor response time, increase the available magnitude of the response, and enhance chemical selectivity. Total pore volume influences the sensor response time and dynamic range. The higher the total pore volume, the longer the time analyte takes to diffuse into the material, thus desirably averaging the sensor response to sudden variations due to turbulence of the flow. Also, the higher the total pore volume, the greater the change in the material property that can occur, thus increasing the available magnitude and available dynamic range of the measurement. In some embodiments of this disclosure, the sensing materials have an open-pore structure that permits a fluid component to move freely or be selectively obstructed from one surface to an opposing surface of the material through a convoluted pathway of interconnecting networked channels.

In some embodiments of this disclosure, the nano-porosity is controlled through a combination of pores engineered into the chemical sensing material 42 and pores that do not pre-exist but are formed in interaction with an analyte.

A combination of permeability and chemical polarity of the functional material cause the material to become chemically sensitive and selective. The present disclosure uses a variety of precursors and derivatization agents to create chemically sensitive materials, which can be polymers, ceramics, silicones, metal oxides, or ferroelectric, magnetic, or composites materials that show an affinity and sensitivity for a particular chemical or class of chemical. The resulting functional materials are designed and optimized for certain properties, such as being hydrophilic, hydrophobic, lyophobic, lyophilic, oleophobic, or oleophilic and their specific affinity for a particular class of chemical.

The specific dielectric constant of the base material can also influence the magnitude of the material property relative to the analyte property and thus the magnitude of the measured response for the specific analyte. For example, in some embodiments, a material of low dielectric constant is preferably used to detect a fluid component of high dielectric constant, and vice-versa.

In addition to the primary selectivity based on matching chemical polarities between the selective material and the chemical component of the analyte fluid within a specific class of chemical such as hydrocarbons of generic chemical formula $C_nH_{2n+2}$, molecular selectivity can be enhanced by selection of the base material porosity so that its pore size matches the desired chemical within the class that is to be detected within the analyte. The base material therefore acts like a sieve, allowing only a certain size molecule or smaller to diffuse into the base material. Thus, a base material can be made or selected with a pore size that would allow, for example, $C_5H_{12}$ (pentane) to diffuse into the material but block the diffusion of $C_8H_{18}$ (octane). Further decreasing of the effective pore size results in natural gas selective materials and stops at the cut-off value of n=1 representing the selectivity for $CH_4$ (methane) only.

The base material therefore can make up the bulk of the sensing material, so its environmental properties can be controlled by the choice of base material and its selectivity can be controlled by the choice of derivatization agents. The two-part nature of the transducer provides independence between basic chemical affinity (sensitivity) and differentiation power (selectivity) of the material, allowing each to be manipulated independently.

In the present disclosure, the thickness of the induction and reader platform 39, the thickness of the sensing material 42, the dimensions and spacing of the electrode fingers 47, and the selective driving of the electrodes 45-46 can be varied to produce an optimal-strength voltage readout from a bridge measurement circuit when excited by a specific input. The output voltage can be proportional to the abundance of the chemical being sensed at a given instant in time.

Figure 10:
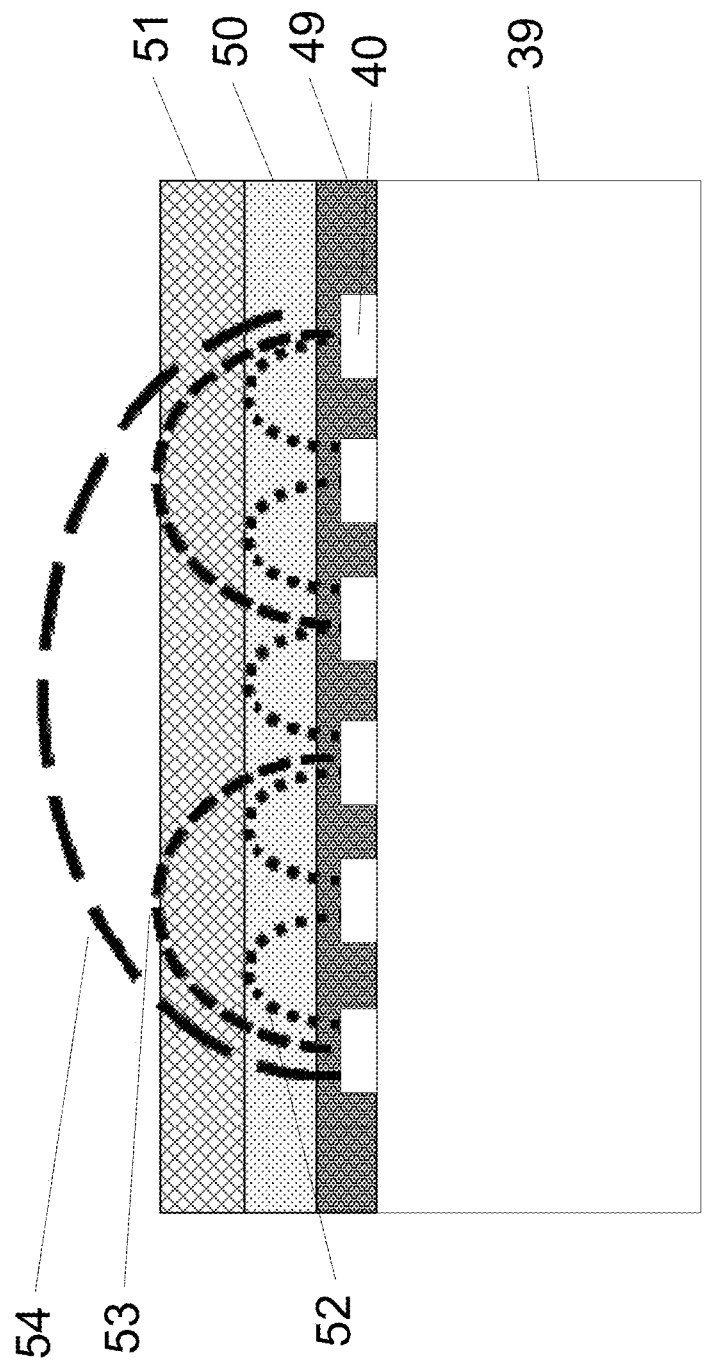
FIG. 10 illustrates a chemical sensor transducer with multilayer structure in accordance with this disclosure.

Both environmental properties and selectivity of the transducer 38 can be further improved by a multilayer structure, as shown in FIG. 10. Each of the selective layers can have an additional functionality. For example, the bottom layer 49 can be impermeable or the least permeable to provide protection from direct contact between the selected fluid component and the substrate and field electrodes 40. The middle layer 50 can be semi-permeable to provide selectivity based on its specific porosity, while the top layer 51 could be the most permeable but pre-selecting the chemicals by its chemical polarity. Alternatively, the middle layer 50 can be of different dielectric relative to that of detected chemical to provide high contrast in the electrical property and of high permeability to generate strong response, while the top layer 51 can serve as a primary selector by chemical polarity.

FIG. 10 also shows that the interdigitated field electrodes 40 enable control of the electrical field protrusion, i.e. from which selective layer to read the signal. In the example shown in FIG. 10, the field 52 from adjacent electrodes penetrates the bottom layer 49 but reaches only up to the middle selective layer 50. The field 53 from the relatively close but not adjacent electrodes, for example every other or interspersed with several electrodes, can penetrate all of the selective layers up to the top layer 51, thus reading the signal composed of all material properties and chemical selected by the materials. Finally, the field 54 generated by distant electrodes protrudes out of the selective materials and provides the signal from the complex fluid mixture above. The field protrusion and overall materials thickness may need to be in a close relation in order to maximize both sensitivity and selectivity of the transducer's response.

In one embodiment, the signal from the field contained with a non-selective material is considered as a reference and the signal from the field reaching out of the selective materials determines the upper limit of the dynamic range for the specific transducer and fluid environment in contact with this transducer.

Figure 11:
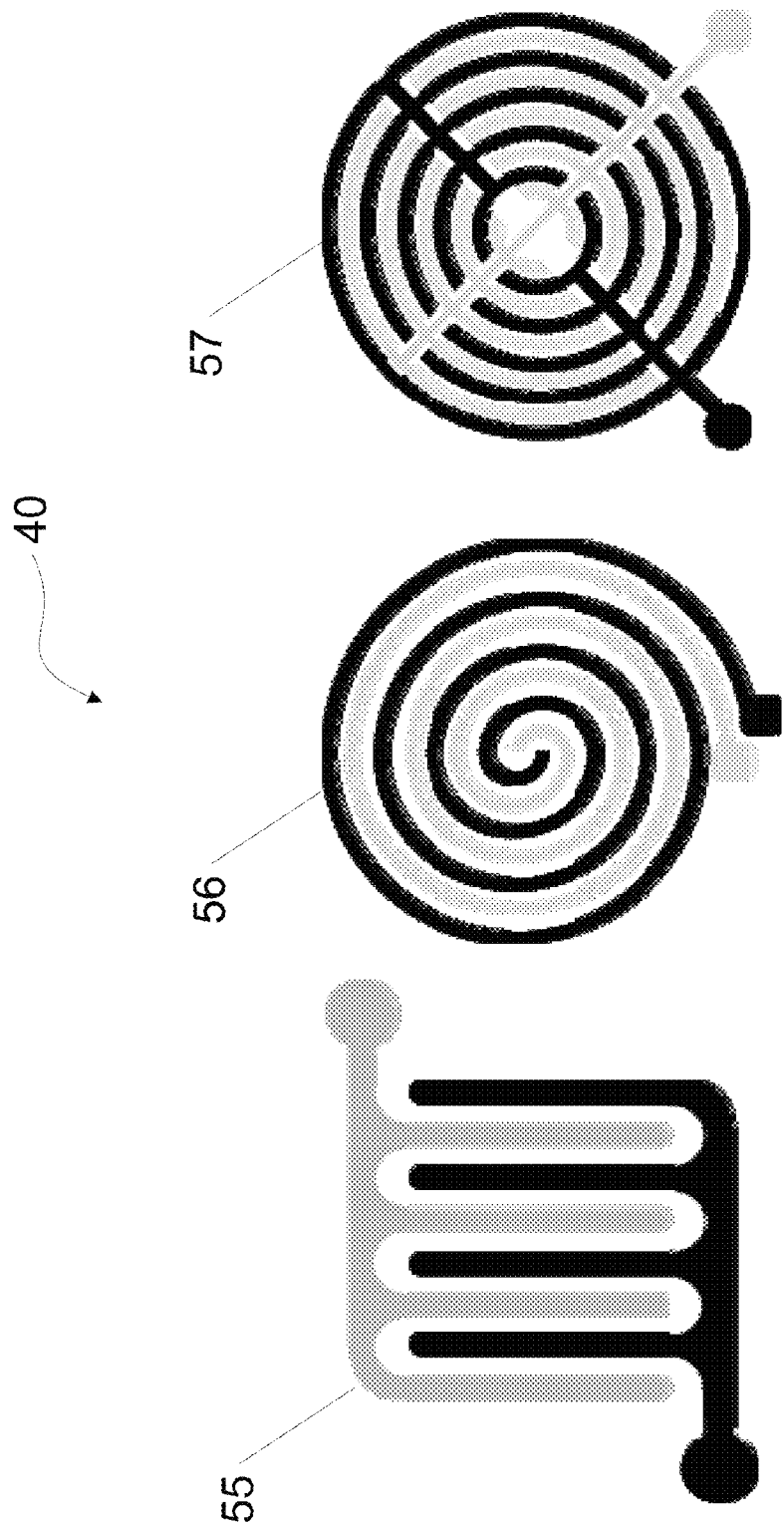
FIG. 11 illustrates alternative electrode designs with rounded geometries in accordance with this disclosure.

The electrical field can be further controlled by the field electrode 40 design, and more specifically by the geometry, distance between the excitation and reading electrodes, and their thicknesses. FIG. 11 shows some examples of geometries with rounded shapes that help to contain the field within the selective materials such as straight interdigital electrode 55, coiled interdigital electrode 56, and a rounded multi-T interdigital 57 electrode. The geometries shown in FIG. 11 are for illustration only. Other geometries may be used without departing from the scope of this disclosure.

Figure 12:
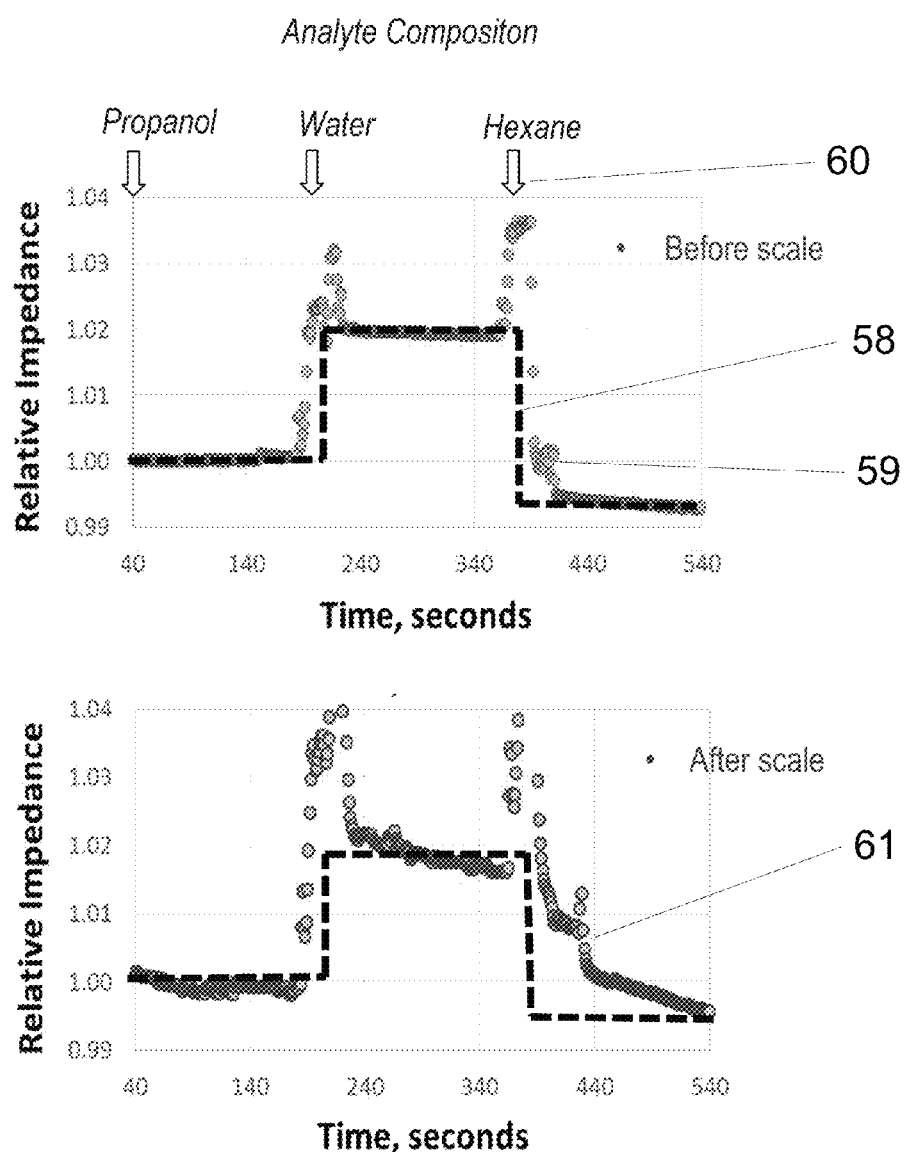
FIG. 12 illustrates an example of chemical sensor performance with fouling present in accordance with this disclosure.
Figure 13:
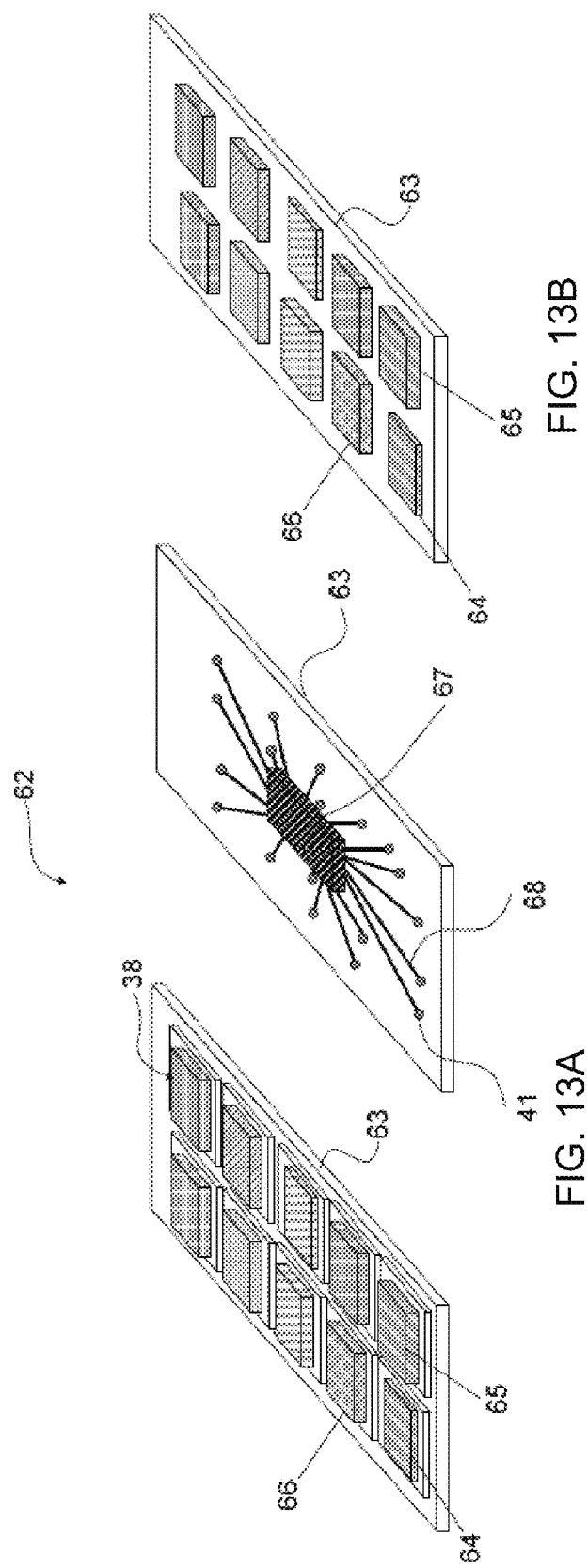
FIGS. 13A-13B illustrate an example chemical sensor transducer array in accordance with this disclosure.
Figure 14:
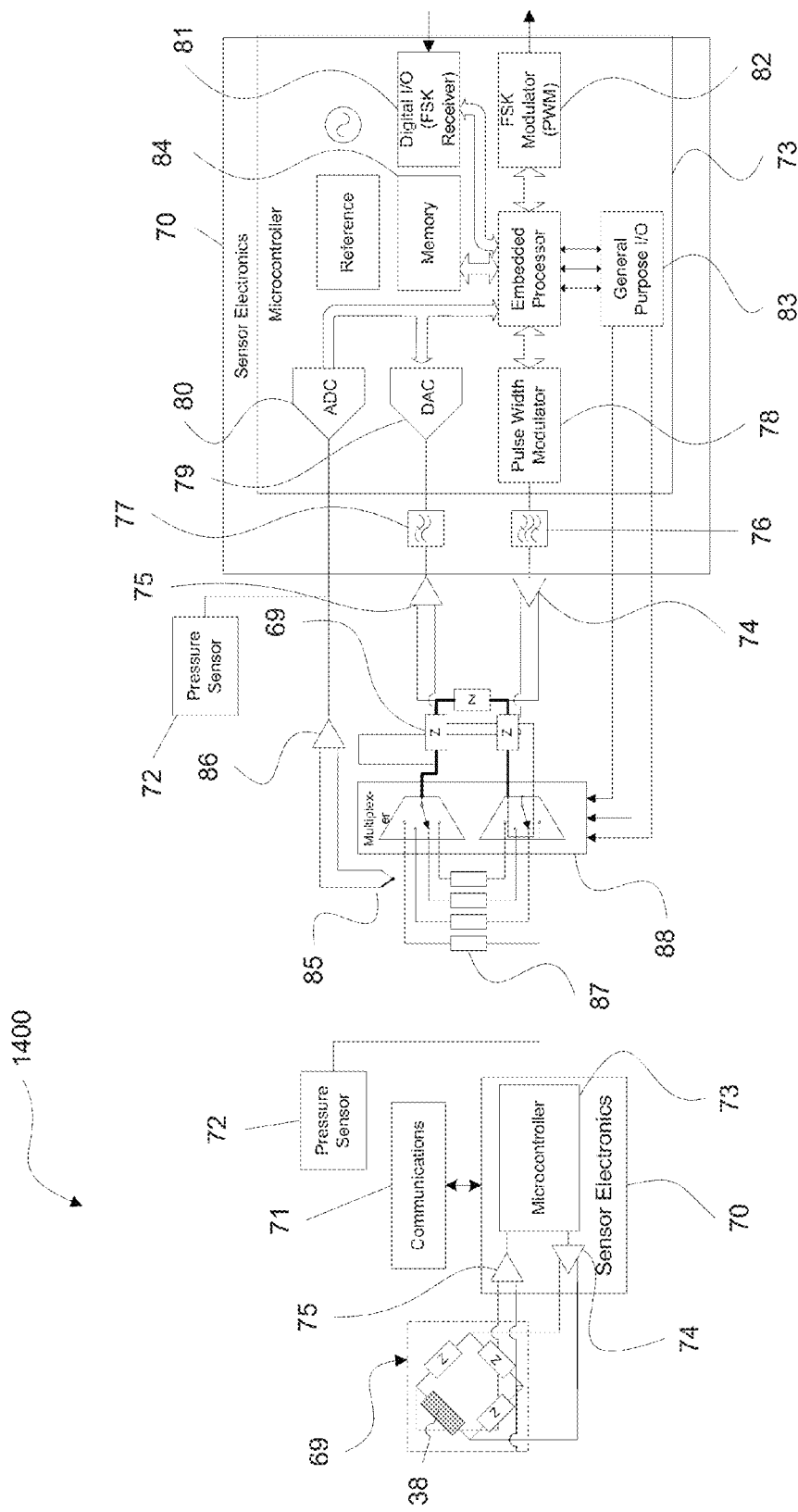
FIGS. 14A-14B illustrate example chemical sensor schematics and electronics in accordance with this disclosure.

The environment found in typical wells may produce material compounds that foul sensors by being deposited on the sensing material, such as inorganic scale, asphaltenes or waxes, which drastically alter their ability to provide accurate measurements if they can measure at all. FIG. 12 shows the projected sensor response 58 and actual sensor response without scale 59 to changes in analyte composition 60 along with the actual sensor response when covered with scale 61 (a 59 mil coating of calcite scale). One effect of the scale deposit is a delay in response as changes in the analyte composition 60 occur. The chemical sensor transducer 38 accomplishes sensing at the molecular level, which makes it particularly insensitive to build up of fouling materials on the surface of the chemical sensing material 42, as the fouling materials are actually porous media with their effective pore sizes much larger that the sizes of the analytes at the molecular level. This porosity allows the analyte to pass through the fouling material to the chemical sensing material 42.

A particular embodiment of the transducer 38 uses a ceramic with a low dielectric constant (such as magnesium aluminum silicate and magnesium silicate compounds) or a material such as quartz glass, cordierite, or borosilicate glass or other similar types of material as the base material. These materials have the ability to withstand high temperatures, high compressive pressures, and abrasion due to a Mhos hardness of 7 or above. Additionally, they possess both ionic and covalent bonding sites, yielding a multiplicity of ways in which the material structure can be manipulated to obtain the desired response. Using a material with a low dielectric constant can improve sensitivity since a smaller concentration of a chemical can be sensed than if a higher dielectric constant material is used. Additionally, a material with a low dielectric constant can provide a low coefficient of thermal expansion, ensuring good adhesion during the temperature changes encountered from manufacturing to in-well usage.

In particular embodiments, the sensing material 42 is initially in the form of a slurry or paste with controlled rheology and is screen-printed or spin coated on the platform 39, which has pre-printed field electrodes 40. This is followed by chemical cross-linking via exposure to radiation, a reagent and/or curing by high-temperature annealing to harden the sensing material 42. Utilization of a thin film fabrication process and micromachining, based on well-defined IC deposition and etching processes, yields high reproducibility and achieves a practical mass production capability allowing multiple transducers 38 of the same sensing material 42 to be manufactured simultaneously.

In other embodiments, the present disclosure uses the ability of electromagnetic fields penetrating into the analyte itself to provide the capability to produce a secondary response type. The secondary response type is based on a comparison of measurements when one measurement is made with the electromagnetic field fully contained within the sensing material 42 and another measurement is made with the electromagnetic field penetrating beyond the sensing material 42. This can be used to enhance the accuracy of the chemical measurement as the signal from outside of the material can be used to normalize the signal from inside of the material for a drift caused by external conditions changes unrelated to the fluid flow composition.

In yet other embodiments, the present disclosure uses differential measurements to provide in-situ calibration of the transducer. The use of this type of electrode may not require controlling the geometry of the transducer sensing material, such as when the sensing material's thickness would ordinarily be controlled to prevent the electromagnetic field from passing substantially outside the transducer itself. Instead, the present disclosure allows controlling the transducer's geometry to vary the dynamic range and response time of the transducer.

To be more useful in a reservoir environment, a chemical sensor could sense more than one chemical, typically in a multiphase flow within the wells of the reservoir. Each chemical typically possesses different concentrations, from very small to very large, as a percentage of the total.

FIGS. 13A-13B illustrate example chemical sensor transducer arrays 62 in accordance with this disclosure. The embodiments of the arrays 62 shown in FIGS. 13A-13B are for illustration only. Other embodiments of the arrays 62 may be used without departing from the scope of this disclosure.

As shown in FIG. 13A, the transducer array 62 allows the sensing of multiple chemicals using different sensing materials, each of them sensitive to a different chemical component of the fluid flow. The mix of sensing materials can be optimized for the specific application. The transducer array 62 includes the induction/reader platform with an array of transducers 38, with multiple sensing materials 64-66 mounted on a motherboard 63 that has backside electronics 67 and interconnects 68. Plated through vias 41 connect the chemical sensor transducers 38 to the backside electronics 67 through the interconnects 68. The sensing materials 64-66 could represent different materials and/or common materials with different thicknesses. Plated through vias 41 provide a signal path from the backside electronics 67 to the field electrodes 40. FIG. 13B shows another embodiment, where the motherboard 63 serves as the induction/reader platform for all the field electrodes 40 in the array, with the multiple sensing materials 64-66 deposited directly on the motherboard 63.

Sensing materials formed from the same material but having different thicknesses create transducers with different saturation points, allowing different maximum concentrations to be sensed. Additionally, the speed of response of a transducer can be affected by the sensing material's thickness. Thicker materials respond more slowly due to the time it takes for an analyte to diffuse significantly into the sensing material and make a material property change measurable. For ultra-thin or nano-particle depositions of sensing materials, the sensitivity increases dramatically when the thickness becomes comparable to the depletion layer thickness of the material. Thus, the array 62 can include sensing materials formed from the same material but having different thicknesses, with at least one thin layer of sensing material providing a quicker response and at least one thick layer of sensing material providing a slower response but extending the concentration range that can be identified.

FIGS. 14A-14B illustrate an example chemical sensor 1400 in accordance with this disclosure. The embodiment of the chemical sensor 1400 shown in FIGS. 14A-14B is for illustration only. Other embodiments of the chemical sensor 1400 may be used without departing from the scope of this disclosure.

Figure 21:
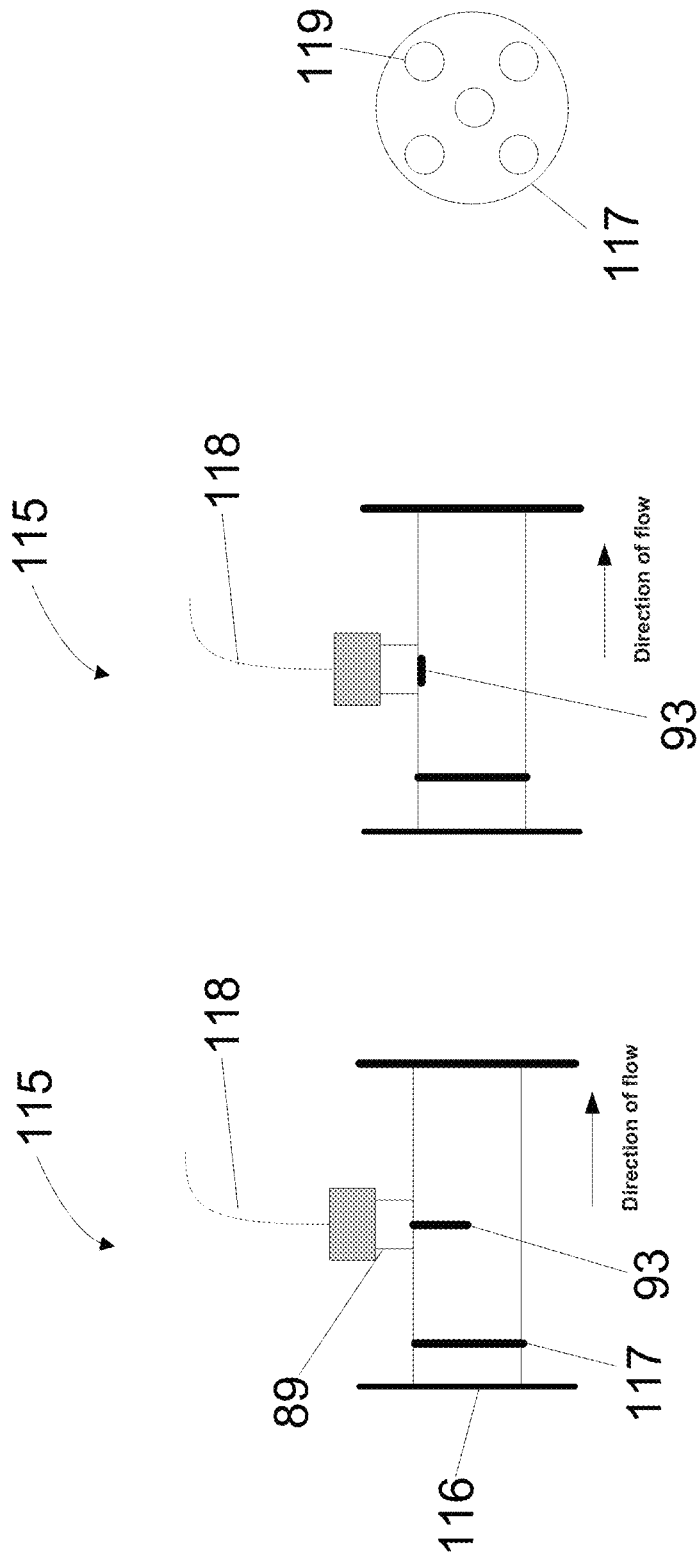
FIGS. 21A-21C illustrate an example surface fluid analyzer for surface applications in accordance with this disclosure.
Figure 22:
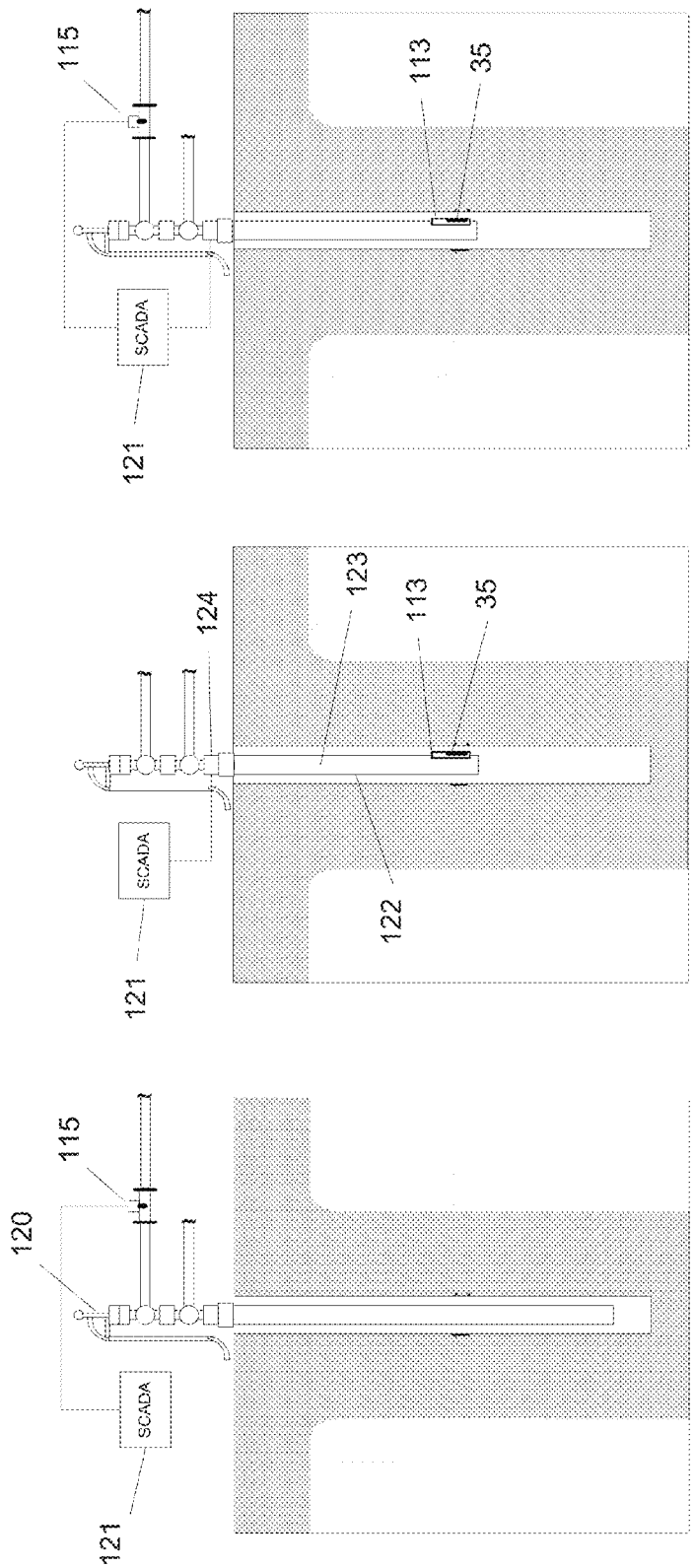
FIGS. 22A-22C illustrate example chemical sensors employed for sensing of an individual well as part of the Production Reservoir Management System in accordance with this disclosure.

As shown in FIG. 14A, the chemical sensor 1400 includes an impedance bridge circuit 69 having the chemical sensing transducer 38, sensor electronics 70, a communication circuit 71, and a pressure sensor 72. The sensor electronics 70 include a microcontroller 73, a driver amplifier 74, and a differential instrumentation amplifier 75. The transducer 38 forms one arm of the bridge circuit 69, allowing changes in its electrical properties to be measured. The impedance bridge circuit 69 can provide noise immunity to the noise-generating environments found downhole. The bridge circuit 69, may be implemented as a two wire circuit as shown in FIG. 14A or as a four wire circuit to further improve accuracy. The pressure sensor 72 may be an absolute pressure sensor type or a differential sensor type to measure differential pressure across a mixing plate 117, which is shown in FIG. 21. The mixing plate 117 provides a restriction in the flow allowing fluid properties (e.g., density and the velocity of the fluid) to be measured and calculated.

The sensor electronics 70 provide both the excitation and sensing of the impedance bridge circuit 69, aided by the differential driver amplifier 74 for excitation and the differential instrumentation amplifier 75 for sensing. The microcontroller 73 provides an analog signal for excitation of the impedance bridge circuit 69 and reads the response of the bridge circuit 69 at the output of the differential instrumentation amplifier 75. The communication circuit 71 can be duplex in nature, relaying information from the sensor to the knowledge engine 2 and relaying commands and reprogramming from the knowledge engine 2 to the sensor. In some embodiments, the communication circuit 71 is a wireless radio for use in surface applications or an acoustic/ultrasonic wireless radio for use in sub-surface applications. Other possible implementations use wired circuitry such as RS-232, RS-485 and Ethernet interfaces. The radio protocol in one implementation is a ZIGBEE protocol, but it may be any radio network, point-to-point, point-to-multipoint, or other wireless protocol (such as IEEE 802.11 or ANT). In particular implementations, the protocol used over the communication circuit 71 is MODBUS, but it may be any other standard or proprietary protocol, such as IPV4, IPV6, UDP, TCP, Fieldbus or HART.

FIG. 14B shows additional details of the sensor electronics 70, which includes an excitation filter 76, a reading filter 77, and the microcontroller 73. The microcontroller 73 may include pulse width modulator (PWM) 78, digital to analog converter 79, analog to digital converter 80, digital input/output 81, FSK modulator 82, general purpose input/output (GPIO) 83, and memory 84. The sensor electronics 70 also include a temperature sensor 85 and a differential amplifier 86 used for temperature compensation. Various components shown outside the microcontroller 73 in FIG. 14B could be integrated into the microcontroller 73. Similarly, various components shown inside the microcontroller 73 in FIG. 14B could be placed outside the microcontroller 73.

The microcontroller 73 provides an analog signal for excitation of the impedance bridge circuit 69 using the pulse width modulator 78, whose frequency and wave shape can be varied via programming in the microcontroller 73. Example excitation frequencies could range from 10 Hz to 10 MHz, and example wave shapes can include sinusoidal, square, triangular, ramp, or narrow pulse shapes or a combination of one or more of these shapes. The frequency and pulse shape may vary in step with each other or independently such that one pulse shape may occur at different frequencies. The excitation filter 76 provides wave shaping to the signal generated by the PWM 78. The temperature sensor 85 can be collocated with an array of transducers 87 so that a calibration of the output of the impedance bridge circuit 69 versus temperature in each transducer 38 can be made if needed. Such calibration may be triggered, for example, due to changes in the sensing material's electrical properties caused by variation in temperature.

In another implementation, the impedance bridge circuit 69, driver amplifier 74, differential instrumentation amplifier 75, excitation filter 76, reading filter 77, and PWM 78 are replaced by an integrated circuit specifically designed to measure complex impedance of a component. The microcontroller 73 then provides the communication functions and controls the integrated circuit.

FIG. 14B also shows that the sensor electronics 70 are used with the array of chemical transducers 87 via multiplexers 88. The multiplexers 88 allow particular transducers 38 with particular sensing materials to be coupled to the remaining components of the impedance bridge circuit 69 at desired times. This reduces the need for separate sensor electronics 70, driver amplifiers 74, and differential instrumentation amplifiers 75 to be provided for each transducer 38 (although this could be done). In other implementations, each transducer 38 could form part of its own impedance bridge circuit 69, and the multiplexers 88 could couple different impedance bridge circuits to the amplifiers 74-75. In the configuration here, a single temperature sensor 85 is used with the array of chemical transducers 87, although separate temperature sensors 85 could be used for each transducer 38. The same or a similar implementation using multiplexers 88 can be used with an integrated circuit specifically designed to measure complex impedance.

Some configurations use comparisons of data when a single sensor of a single sensing material is operated over a range of frequencies to maximize conductivity of the sensing material. This may be a time consuming process, taking hundreds of microseconds for each measurement. It may place strict property matching requirements on each arm of the multiplexers 88 to switch the sensing material, or it may require a complex calibration procedure. Since materials and circuits drift differently with application of high temperatures and pressures and since they cannot be truly physically collocated, significant errors might be introduced with this method.

The present disclosure, while capable of operating over a range of frequencies, can also operate at a single frequency/measured parameter combination that is optimized for each specific transducer patch. This can provide increased measurement speed and reduced calibration requirements. The specific measured parameter, capacitance, inductivity, resistivity, resonance, or other chemically-affected property can be chosen to provide the highest output from the bridge circuit to produce the best signal-to-noise ratio (SNR) possible in the noisy environment of a well. This combination of measured parameter and frequency can be specific to the sensing material and chemical to be detected. There may also be cases in which multiple combinations of parameter measured and frequency produce acceptable results for the same material, but there is often only one combination that produces optimum results for a given sensing material thickness.

Figure 15:
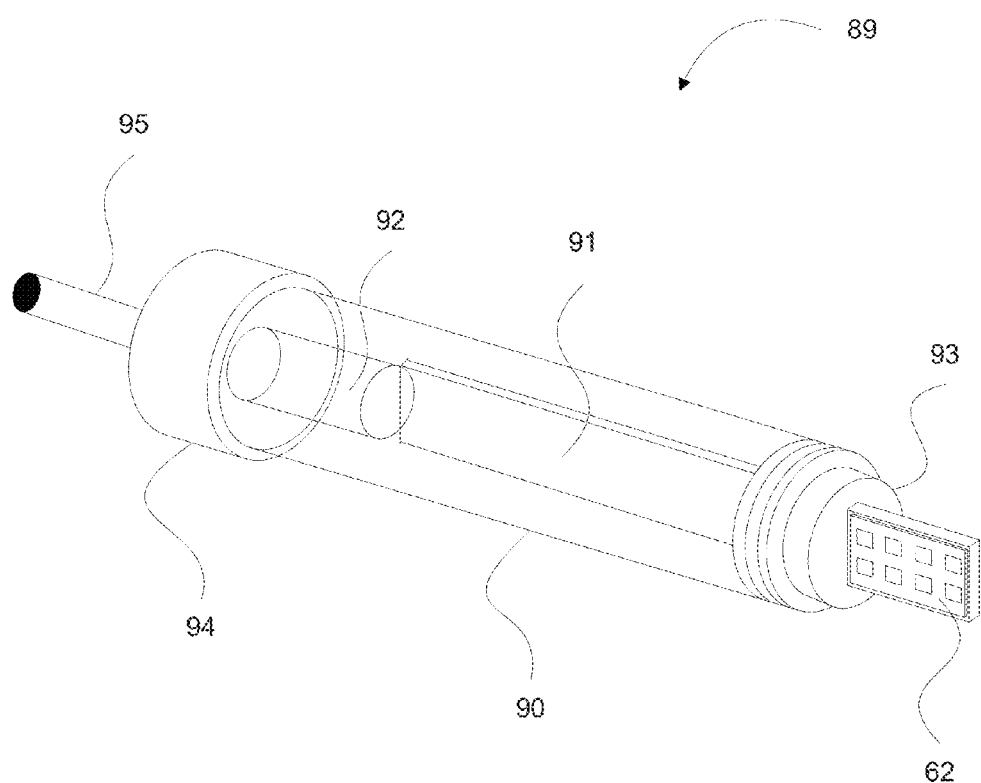
FIG. 15 illustrates an example surface fluid analyzer chemical sensor in accordance with this disclosure.

FIG. 15 illustrates an example surface fluid analyzer chemical sensor 89 in accordance with this disclosure. The embodiment of the surface fluid analyzer chemical sensor 89 shown in FIG. 15 is for illustration only. Other embodiments of the surface fluid analyzer chemical sensor 89 may be used without departing from the scope of this disclosure. In some embodiments, the surface fluid analyzer chemical sensor 89 may represent the chemical sensor 1400 shown in FIGS. 14A-14B.

The chemical sensor 89 here could be used in a wellhead or other surface location. The sensor 89 includes a tubular housing 90, which contains a sensor electronics board 91 and a power supply 92. A transducer array assembly 93 is located at one end of the tubular housing 90, and a closed cap 94 is located at the other end of the tubular housing 90. A connection 95 for external communications extrudes through the cap 94. The housing 90 can be made of any suitable material(s), such as stainless steel, and can have any suitable standard or non-standard size. The size can be chosen to match the size of logging tools so that the internal components can also be used for chemical sensing as part of a logging tool.

The housing 90 can be threaded at one or both ends. For example, the bottom end can be internally threaded to accept the transducer array assembly 93 while making a liquid- and gas-tight seal with or without the use of O-rings. The bottom end can also be externally threaded to allow it to be screwed into a production pipe section, which positions the transducer array assembly 93 in the production flow. The top end of the housing 90 can be externally threaded to allow the cap 94 to screw onto the housing 90 and seal the housing against the elements. The cap 94 also provides easy access for replacement of parts within the housing 90, such as the power supply 92 (which may be a battery or a power converter for an external source). The connection 95 is located through the cap 94. If wireless communications are utilized in the unit, an antenna may be directly connected to the connection 95, or a socket may exist if wired communications are used. Alternately, the connection 95 may host a direct connection to a data storage device, such as a hard drive or a USB or other solid-state drive.

Figure 16B:
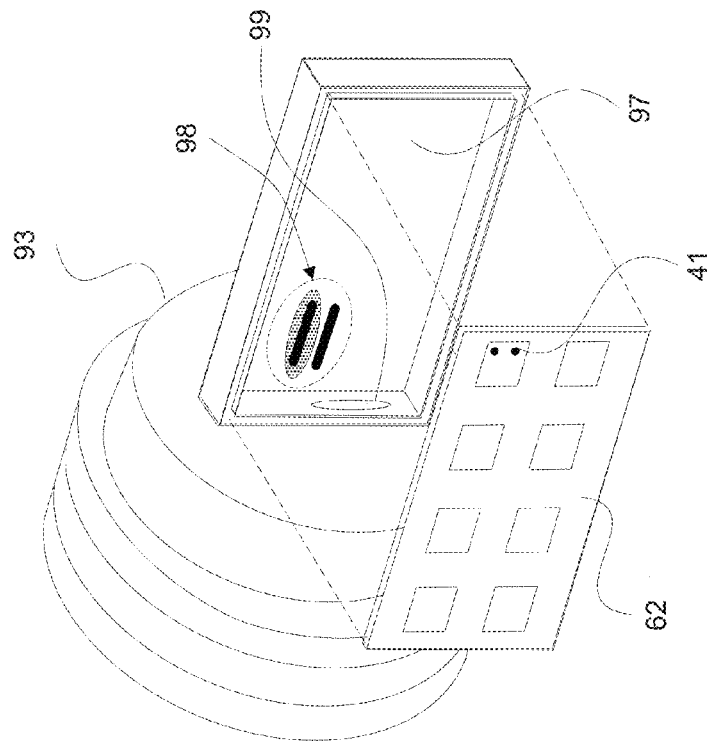
FIGS. 16A-16B illustrate an example transducer array assembly in the surface fluid analyzer chemical sensor in accordance with this disclosure.
Figure 16A:
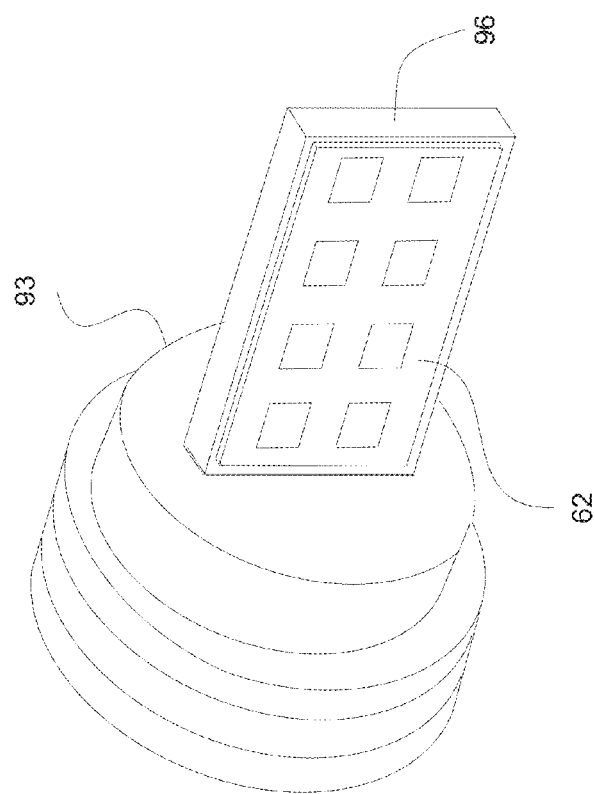

FIGS. 16A-16B illustrate an example transducer array assembly 93 in the surface fluid analyzer chemical sensor 89 in accordance with this disclosure. The embodiment of the transducer array assembly 93 shown in FIGS. 16A-16B is for illustration only. Other embodiments of the transducer array assembly 93 may be used without departing from the scope of this disclosure.

FIG. 16A shows the transducer array assembly 93 with an array housing 96. FIG. 16B shows an exploded view of the transducer array assembly 93. An array housing cavity 97 serves to protect the electronics that it contains, and connections may pass through a slot 99. This allows connection to the electronics using, for example, a flexible interconnect cable or individual wires. A hot wire flow sensor 98 can be embedded in the array housing 96. The hot wire flow sensor 98 provides flow rate input so that, when coupled with the known diameter of the pipe in which the sensor is placed, a chemical concentration can be calculated from the abundance measurement the array provides. This calculation could take place in the microcontroller 73. Alternately, the flow sensor could be implemented as a spinner, turbine, or other type of flow sensor instead of the hot wire type. Any of these implementations can be placed outside of the array housing 96, such as in a location in the main pipe of the flanged nipple assembly 116 shown in FIG. 21A.

The use of filled plated through vias 41, which are covered by sensing material 42 to make electrical connections with backside electronics 67, allows the chemical sensor transducer array 62 to be sealed to the array housing 96. Taken in its entirety, the backside electronics 67 are completely shielded from the environment. Flat surfaces can ensure the ability to achieve an excellent bond without leaks. Thus, only the topside of the array 62 and the array housing 96 itself are exposed to the environment. Both structures can be made from materials that can withstand the temperatures, pressures and chemically caustic environments downhole. This provides the capability to operate the sensor in harsh environments while ensuring operational reliability of the electronics.

Figure 17:
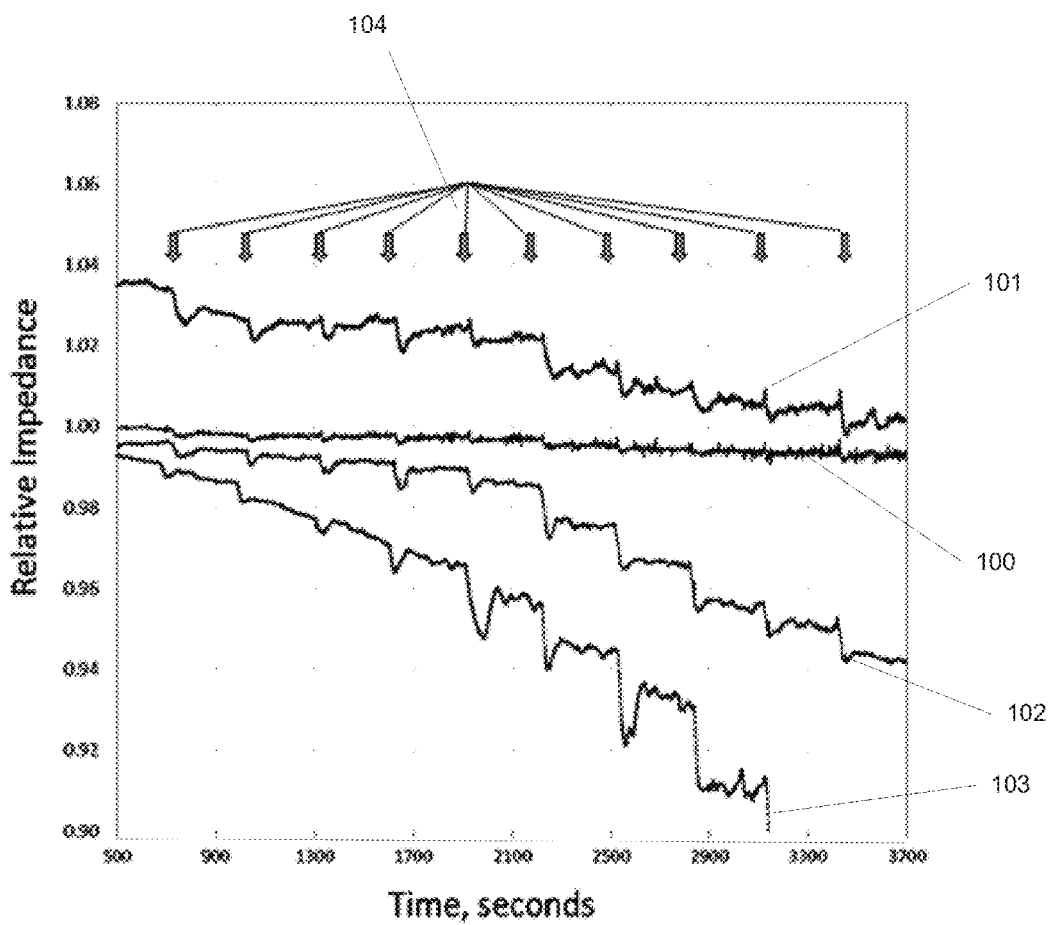
FIG. 17 illustrates multiple sensor chemical sensing data in response to a multistep analyte fluid change over time in accordance with this disclosure.

In a specific embodiment, optimized transducers 38, each selective to different relevant components of a complex fluid, are arranged into an array 62, where one of them is intentionally non-selective to serve as a reference, a second one is selective to hydrocarbons to provide an oil-sensitive response, a third one is selective to water, and a fourth one is sensitive to the salinity level in the aqueous phase. FIG. 17 shows the set of four data traces from measurements of such a transducer array 62, the reference response 100, oil-sensitive response 101, water sensitive response 102, and salinity level in the aqueous phase response 103. Each of the transducers responds selectively to the fluid component they were designed for, and promptly follow the injections of brine into a stirred oil 104, equilibrating after the multiphase mixture becomes well mixed.

Figure 18A:
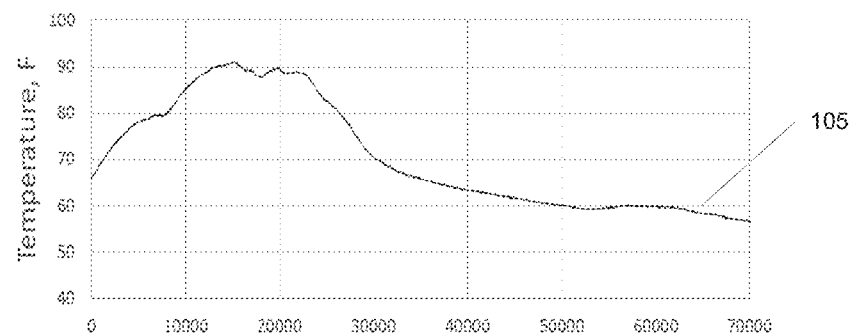
FIGS. 18A-18C illustrate sensor performance with respect to temperature of a chemical in accordance with this disclosure.
Figure 18B:
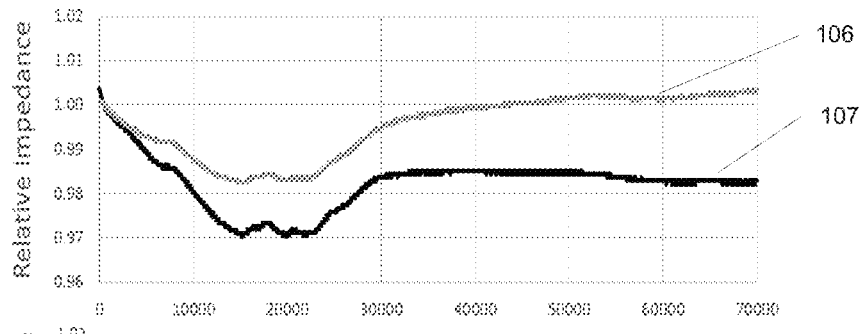
Figure 18C:
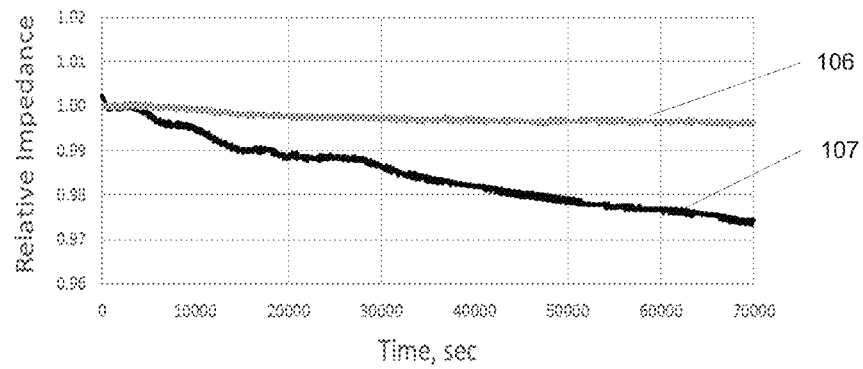

In another embodiment, an optimized array of transducers 62 is installed at an example wellhead in the Permian Basin with limited production of crude oil and gas, contacted by gas only with an increasing level of moisture at varying temperature. Temperature is one of the environmental parameters that affects the transducer's 38 response. FIGS. 18A-18C show the individual measured response traces from this transducer array collected across a single day. The temperature trace 105 in FIG. 18A shows an example daily variation of temperatures at an example wellhead at Permian Basin. As shown in FIG. 18B, two transducer traces, one being a chemically non-selective transducer trace 106 and the other being a water sensitive transducer trace 107, provide an mirror image of the temperature profile. After the temperature normalization, the reference trace becomes flat, while the water-selective transducer monitors the increasing moisture level as shown in FIG. 18C.

As an alternative to using an independent temperature sensor and the post-detection temperature compensation, the interdigitated electrode design provides a method for active temperature control directly at the transducer, with one of the electrodes with an optimized resistance serving as a heater and the whole non-selective transducer serving as a temperature sensor. The temperature response can immediately be used to tune the power for the heating element, so the resulting temperature is kept constant regardless of the environmental temperature.

Figure 19:
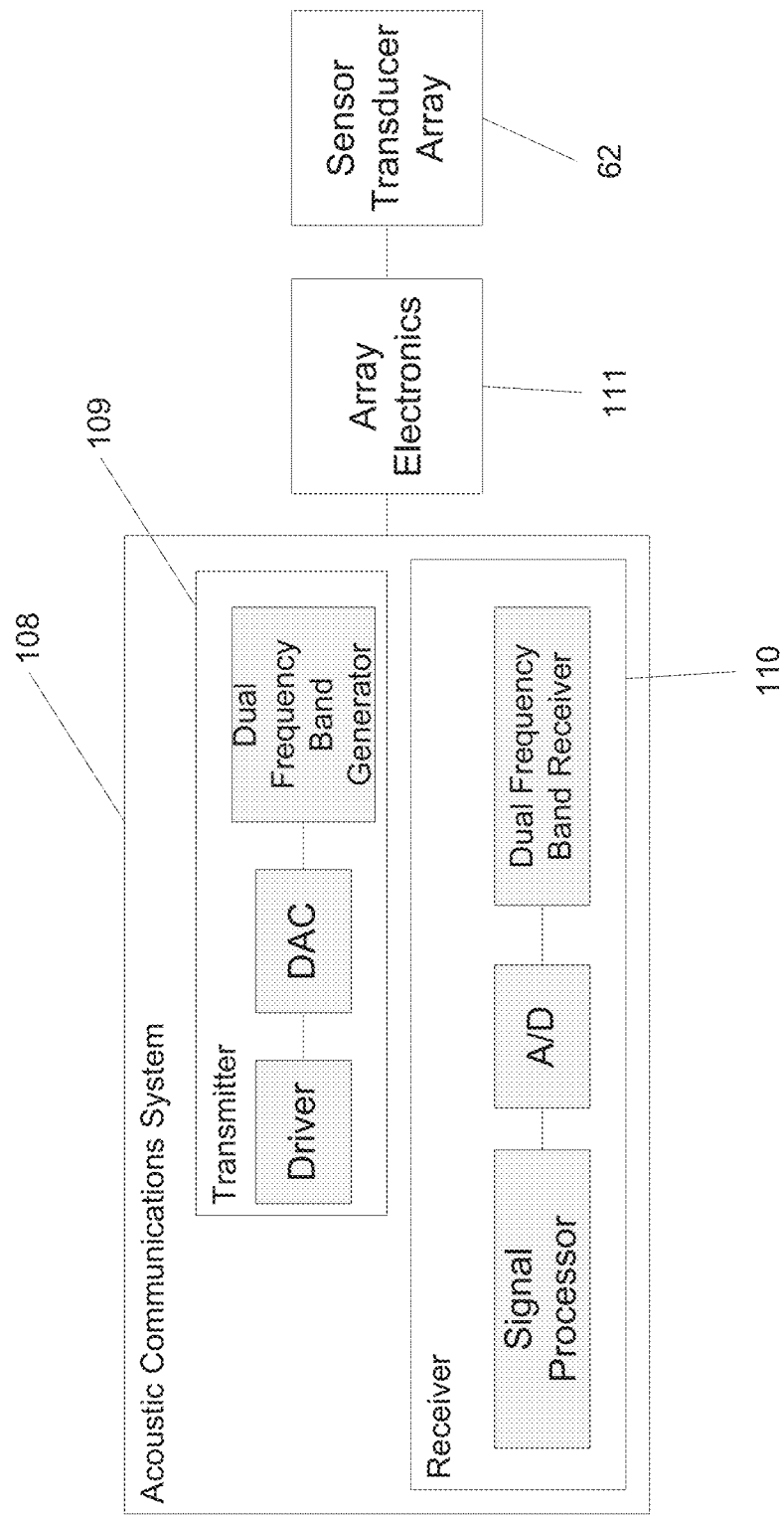
FIG. 19 illustrates an example acoustic communication system for use with a chemical sensor in sub-surface applications in accordance with this disclosure.

FIG. 19 illustrates an example acoustic communication system 108 for use with a chemical sensor in sub-surface applications in accordance with this disclosure. The embodiment of the acoustic communication system 108 shown in FIG. 19 is for illustration only. Other embodiments of the acoustic communication system 108 may be used without departing from the scope of this disclosure.

The acoustic communication system 108 employs a transmitter 109 and a receiver 110, which could collectively form a transceiver. The transceiver is electronically connected to array electronics 111 to provide for communications of data from the sensor array 62, as well as for commanding and reprogramming the sensor. A dual-frequency transceiver could be used, with one band including higher ranges of an acoustic band and the other band including an ultrasonic band.

In subterranean applications, transmitted and received signals travel through confined fluids, which may contain pockets or slugs of trapped gases, as well as through sections of pipe that are coupled together. The pockets of gas and the coupling sections of pipe disturb the communications, making them less reliable and lowering the available data rate due to interference. Dual-band transmissions can help to provide reliable transmissions while maintaining a higher data rate since the different frequency bands have different properties with respect to the electromagnetic index of refraction. Thus, while the acoustic band is "bent" more by a gas pocket (causing significant multipath interference), the ultrasonic band is "bent" less, so it causes less multipath interference and increases the reliability of the transmission. The opposite is true in the case of a pipe coupling, where the size of the coupling is more significant in relation to the wavelength of the ultrasonic band than to the acoustic band.

Figure 20:
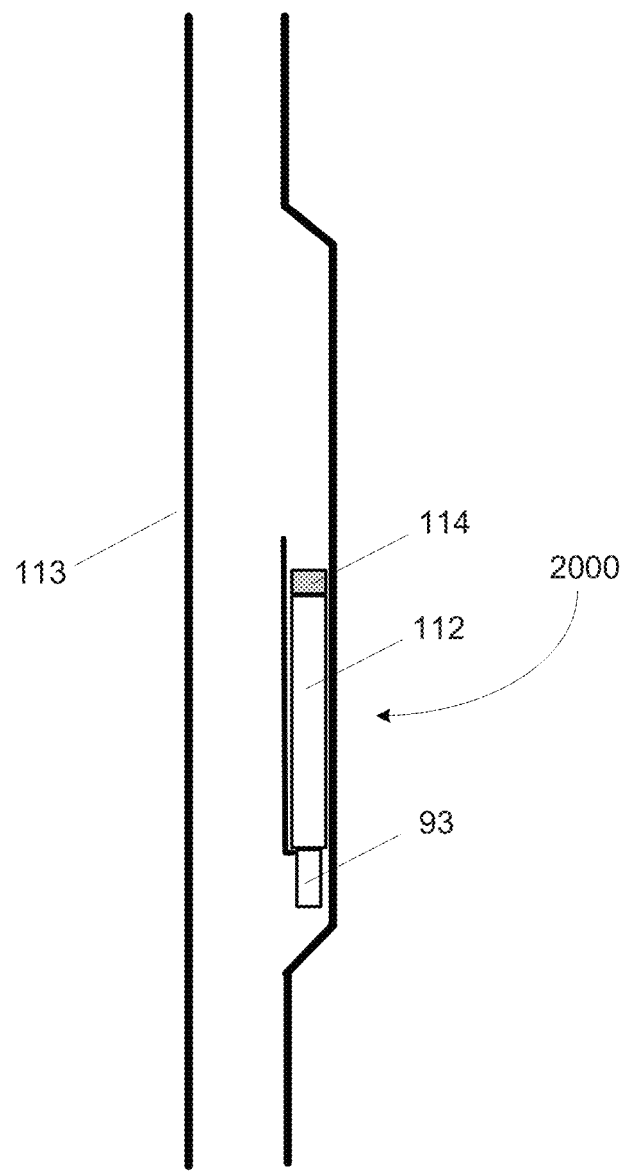
FIG. 20 illustrates an example chemical sensor in a sub-surface application in accordance with this disclosure.

FIG. 20 illustrates an example chemical sensor 2000 in a sub-surface application in accordance with this disclosure. The embodiment of the chemical sensor 2000 shown in FIG. 20 is for illustration only. Other embodiments of the chemical sensor 2000 may be used without departing from the scope of this disclosure. In some embodiments, the chemical sensor 2000 may represent the chemical sensor 1400 shown in FIGS. 14A-14B or the surface fluid analyzer chemical sensor 89 shown in FIG. 15.

In this example, a housing 112 of the chemical sensor 2000 resides within a side pocked mandrel 113 that has been inserted in the production string (such as with a SLICKLINE using standard methods). The mechanical configuration positions the transducer array assembly 93 so that it is immersed in the fluid or gas flow, and a communication interface 114 (such as system 108) is able to communicate up the pipe. The mechanical configuration is similar to that of FIG. 15, with the closed cap 94 containing the communication interface 114.

FIGS. 21A-21C illustrate an example wellhead fluid analyzer 115 for surface applications in accordance with this disclosure. The embodiment of the wellhead fluid analyzer 115 shown in FIGS. 21A-21C is for illustration only. Other embodiments of the wellhead fluid analyzer 115 may be used without departing from the scope of this disclosure.

In FIG. 21A, the wellhead fluid analyzer (WFA) 115 includes a flanged nipple assembly 116, a surface chemical sensor 89, and a mixing plate 117. The surface chemical sensor 89 is inserted so that its transducer array assembly 93 is placed vertically in the fluid or gas flow. The transducer array assembly 93 is positioned so that the flow is parallel to the face of the individual transducers to minimize the probability of the transducers being struck by objects embedded in the flow, such as rocks. The transducer array assembly 93 can also be positioned such that it directly impacted by the flow, turned so that it is facing away from the flow, or positioned at any angle in between as may be advantageous. Since the diameter of the main pipe of the flanged nipple assembly 116 of the WFA 115 is fixed and known, each chemical's concentration can be computed in the sensor for forwarding to the knowledge engine 2. A communications connection 118 is attached to the surface chemical sensor 89. The connection 118 supports a hardwired connection to a data exfiltration system, such as a supervisory control and data acquisition (SCADA) system or other system. In other embodiments, a wireless radio is used in the surface chemical sensor 89, and an antenna is instead attached to the surface chemical sensor 89.

FIG. 21B shows another embodiment in which the sensor's mechanical configuration has been altered to make the transducer array assembly 93 parallel to the fluid flow. The mixing plate 117 stirs the flow to provide a homogeneous flow instead of a laminar flow to ensure the accuracy of the sensing. If a single sensor is placed in a laminar flow, placement of the sensor would determine what chemicals could be found, as only those chemicals that were in the strata in which the sensor is placed would be sensed. Multiple sensor placements at different relative positions around the perimeter can then provide information on phase-separated streams of different fluid components, for example gas flowing on top, oil in the middle and aqueous phase at the bottom of the stratified production flow.

FIG. 21C shows an example mixing plate 117, which represents a solid plate with holes 119. In other embodiments, the mixing plate could be replaced with a ramp or a set of tubes that are twisted together.

Chemical Sensor Networks & Management Systems

The PRMS 1000 uses inputs from chemical sensors to provide data for the knowledge engine 2. Current methods and apparatuses often include a test separator, which provides an oil, gas and water ratio but operates at atmospheric temperatures and pressures. This can cause inaccuracies in measurements due to exceeding the bubble point for gases, precipitation due to saturation as temperature decreases, and other similar physical phenomena. Sampling chemical sensors operate at well pressures and temperatures but do not provide continuous information. The present disclosure's chemical sensors operate in a continuous manner at well pressures and temperatures, providing continuous information directly about well conditions. This allows even rapidly-changing conditions to be measured and information to be provided to the system user.

FIGS. 22A-22C illustrate example chemical sensors employed for sensing of an individual well as part of a Production Reservoir Management System in accordance with this disclosure. The embodiments shown in FIGS. 22A-22C are for illustration only. Other embodiments may be used without departing from the scope of this disclosure.

In FIG. 22A, a fluid analyzer 115 with a chemical sensor is employed for surface sensing of an individual well's flow. The fluid analyzer 115 is placed in the production flow path of wellhead equipment 120, and the fluid analyzer 115 provides data to a SCADA system 121 or other data exfiltration system. This embodiment is useful for wells with a single production zone, and it can also be used to obtain an overall operational picture of a well with multiple producing zones.

In other embodiments, such as shown in FIG. 22B, a chemical sensor 35 is placed in the mandrel 113 as part of a production string pipe 122. This places the sensor directly in the fluid flow 123 at a point with a known pipe diameter. This embodiment is useful in wells having more than one active production zone. Since the pipe diameter is known, a simple flow measurement allows the calculation of chemical concentrations. A wellhead transceiver 124 can be placed in the wellhead equipment to allow extraction of data transmitted from the chemical sensor using the communication system 108.

FIG. 22C shows a combination of both sensors from FIGS. 22A and 22B. Here, both surface and subterranean sensing in the same well is supported by the PRMS.

Figure 23:
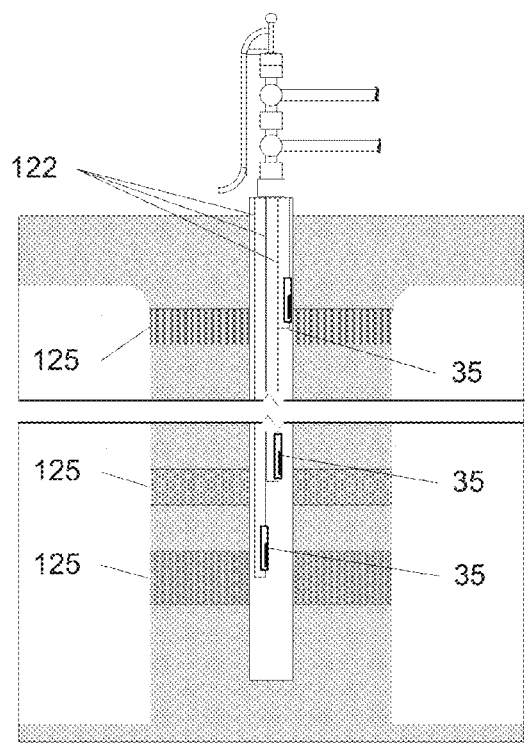
FIG. 23 illustrates an example chemical sensor placement for a well having a multiplicity of production zones using a multiplicity of downhole sensors in accordance with this disclosure.

FIG. 23 illustrates an example chemical sensor placement for a well having a multiplicity of production zones 125 using a multiplicity of downhole sensors 35 in accordance with this disclosure. The embodiment shown in FIG. 23 is for illustration only. Other embodiments may be used without departing from the scope of this disclosure. Here, a chemical sensor 35 is placed in each zone so that information can be obtained from each of the producing zones of interest. If a zone is packed off, no sensor is required, as it is not producing.

Figure 24:
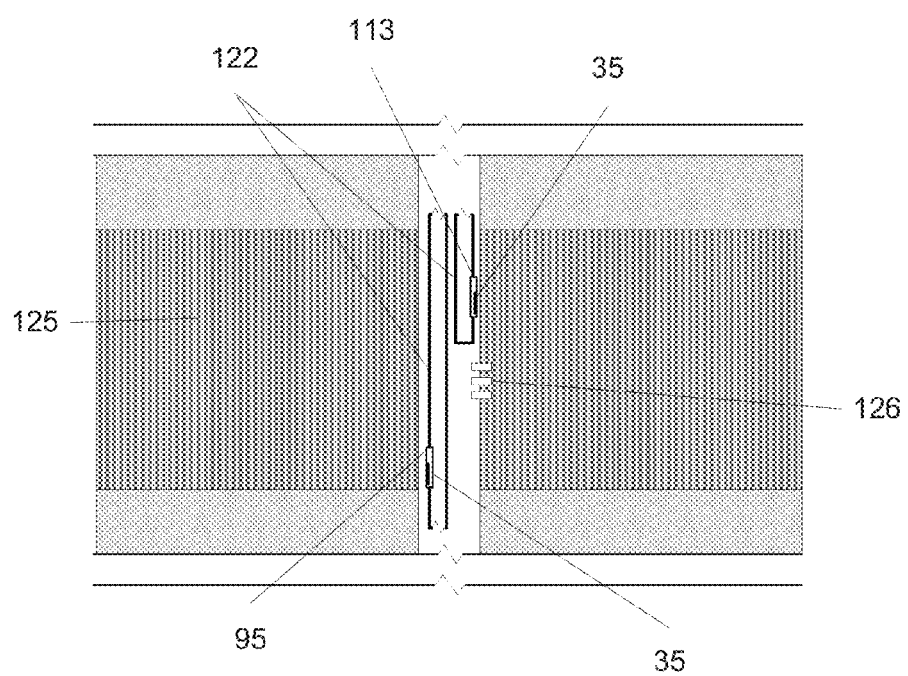
FIG. 24 illustrates an example chemical sensor placement for a production zone which has been perforated with a set of perforations in accordance with this disclosure.

FIG. 24 illustrates an example chemical sensor placement for a production zone 125, which has been perforated with a set of perforations 126 in accordance with this disclosure. The embodiment shown in FIG. 24 is for illustration only. Other embodiments may be used without departing from the scope of this disclosure.

Again, the sensors 35 are placed in side mandrels 113 within production string pipes 122. As can be seen in FIG. 24, the sensors 35 are placed above and below the perforation(s) of interest. For determination of specific chemical information from a specific production zone 125, the difference between the compositions measured by the two sensors 35 can be compared. This can be done for all producing zones, and chemical sensors 35 can be placed above and below each producing zone for all but the lowest zone. This information can be processed by the knowledge engine 2 to extract zone-specific analyses for each zone. Further, information about all wells in the reservoir can be captured using WFAs 115 or subterranean emplacements and can be processed by the knowledge engine 2 to provide an overall operational reservoir picture. This can include, but is not limited to, topographical analysis on a chemical by chemical basis, sweep effectivity for injection sweeps commonly used in EOR, and well to well communication.

Figure 25:
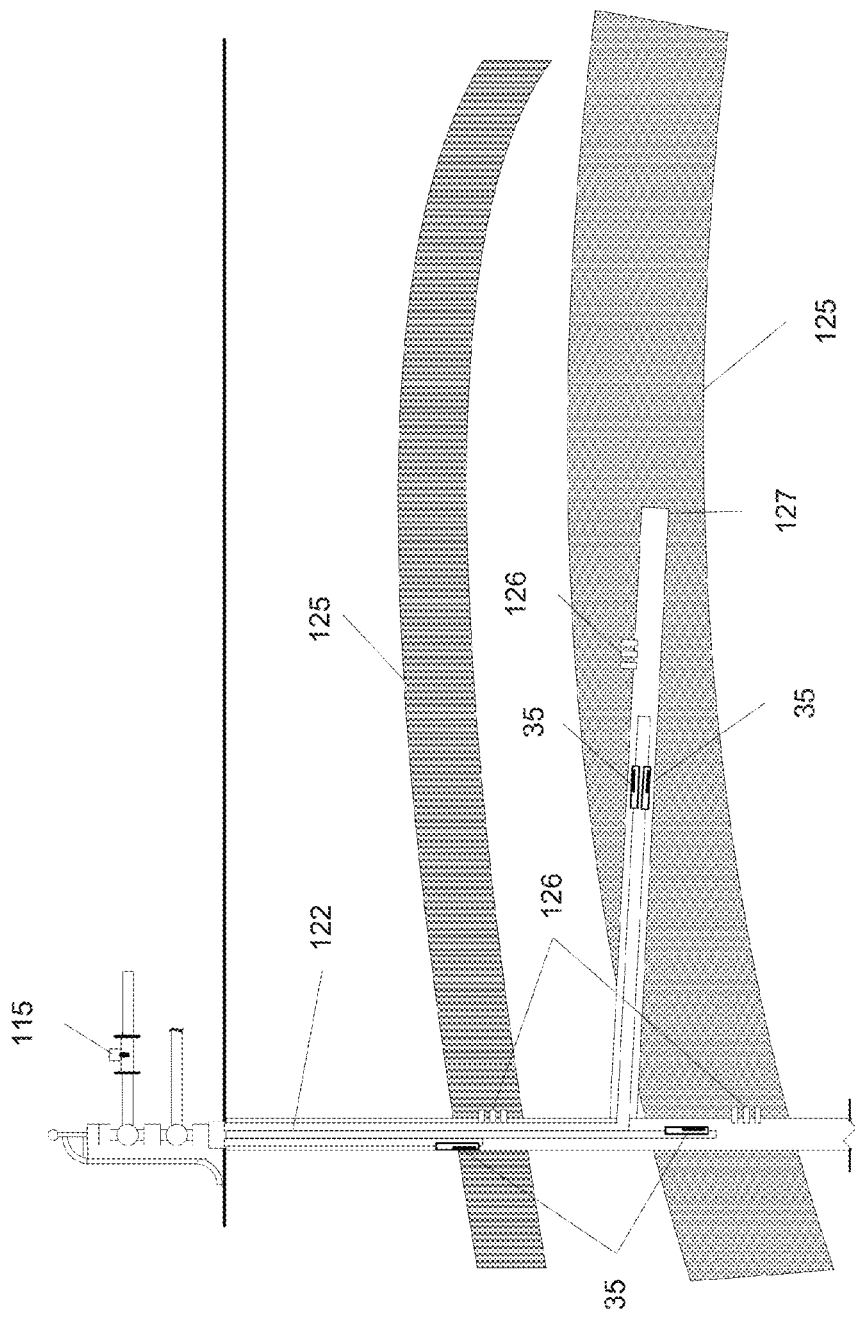
FIG. 25 illustrates example sensor placements in a well with multiple zones including a horizontal well bore in accordance with this disclosure.

FIG. 25 illustrates example sensor placements in a well with multiple zones 125 including a horizontal well bore 127 in accordance with this disclosure. The embodiment shown in FIG. 25 is for illustration only. Other embodiments may be used without departing from the scope of this disclosure.

Sensors 35 can be placed inside the bore 127. Two or more chemical sensors 35 can also be placed so that they span the vertical height of the horizontal well bore 127 (or production string pipe 122, if present) since laminar flow is typical in horizontal bores and the various phases of the flow would separate out due to their different specific gravities. The placement of multiple chemical sensors 35 ensures an accurate determination of chemical concentrations can be made. Alternately, a single linear array of any number of chemical sensor transducers 38 can be assembled into a single chemical sensor 35 to span the horizontal bore 127.

Figure 26A:
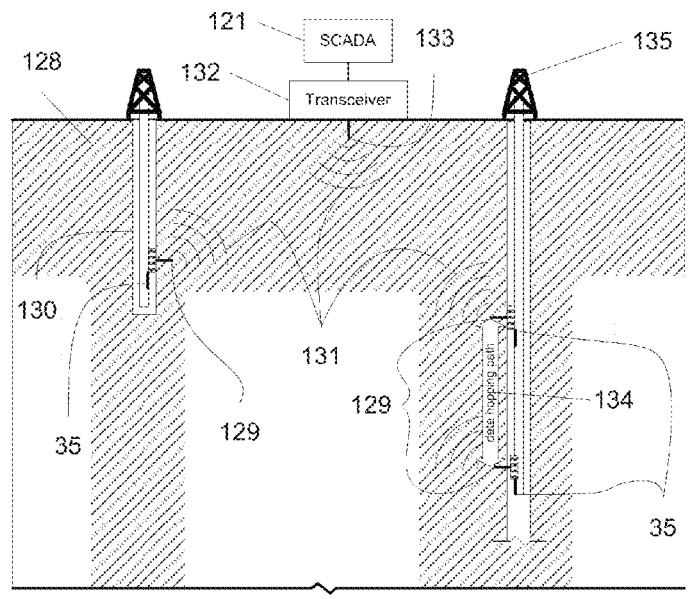
FIGS. 26A-26B illustrate example earthmode transmissions for closely (locally) located wells and wells that are beyond the subterranean communications range in accordance with this disclosure.
Figure 26B:
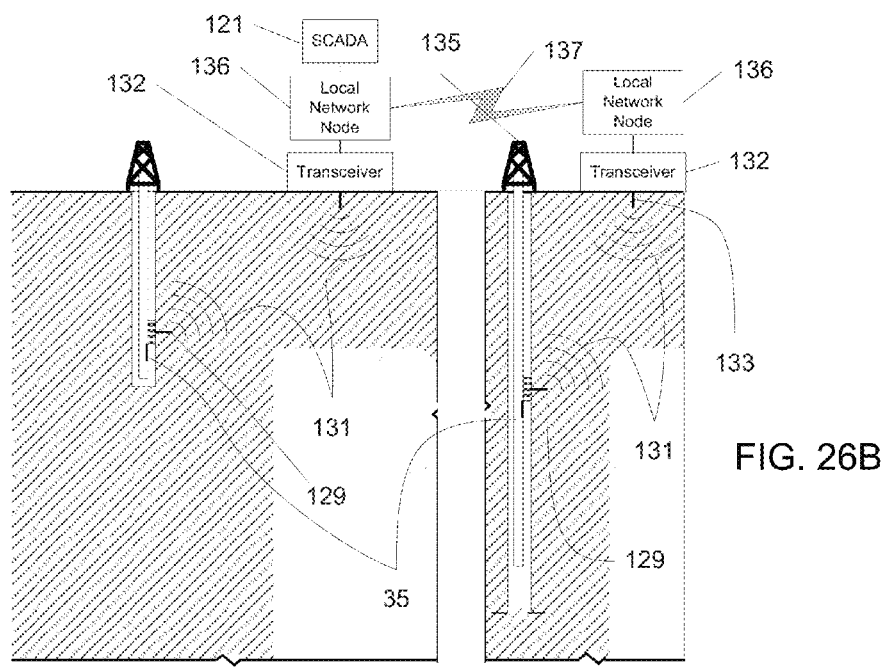

FIGS. 26A-26B illustrate example earthmode transmissions for closely (locally) located wells and wells that are beyond the subterranean communications range in accordance with this disclosure. The embodiments shown in FIGS. 26A-26B are for illustration only. Other embodiments may be used without departing from the scope of this disclosure.

These embodiments use portions of the earth 128 (earthmode) as a transmission medium for closely located wells and for wells that are beyond the subterranean communications range. Here, a chemical sensor 35 is connected to an earth-mode radio and antenna 129 that are embedded into the earth 128 in the side of a wellbore 130. An electromagnetic signal 131, such as in the acoustic or ultrasonic range, is relayed through the earth 128 to establish communications with a surface transceiver 132 located on the surface, but having its antenna 133 embedded in the earth to form a wireless underground sensor network (WUSN). Communication frequencies are not limited to the acoustic or ultrasonic range, and other frequencies (such as high as the 169 MHz bands) can be useful with a more limited range. This range may be more appropriate for intra-well communication hopping 134, which relays a signal up the wellbore 130 from one sensor radio and antenna 129 to another where it is regenerated to maximize the SNR of the signal before being retransmitted. The final hop of the network is between the radio and antenna 129 and the surface transceiver 132 and its antenna 133, minimizing the transmitter power requirements. The surface transceiver 132 is attached to a SCADA communication system 121 or other system for communications external to the reservoir.

The transceiver 132 can also communicate with additional wells 135 within signal propagation range. FIG. 26B shows an embodiment when communications for some wells are outside of direct in-earth signal propagation range. Wireless local area network nodes 136 are added to establish communication links 137 using air as the transmission medium.

Note that in the description above, reference is made to "continuous" measuring, monitoring, or other operations. In other embodiments, near-continuous measuring, monitoring, or other operations could be used to obtain the same or similar benefits described above.

Although these figures illustrate examples of devices, systems, and methods for reservoir and well management based on direct in-well chemical measurements, various changes may be made to any of these figures. For example, the structural arrangements of various devices and systems are for illustration only. Various components in each figure could be moved, combined, further sub-divided, or omitted and additional components could be added according to particular needs. Also, a component or group of components in a figure could be replaced by another component or group of components that performs the same or similar function.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "fluids" may include liquids, gases, or any combination thereof.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system for well and reservoir management for optimized production of fluids in a reservoir, the system comprising:
    a knowledge engine configured to receive a plurality of field inputs, process and analyze the field inputs, and provide a plurality of data outputs for presentation to an operator; and
    a user data interface configured to display the plurality of data outputs,
    wherein the plurality of field inputs comprises (i) dynamic, continuously measured chemical sensing data supplied by at least one chemical sensor installed into surface equipment at a wellhead at a well, (ii) at least one of: temperature, pressure, flow rate and concentration of production components from one or more individual wells located within the reservoir, and (iii) at least one of: seismic surveys of the reservoir, permeability, geochemistry and lithology of rock formations, and geographic information system (GIS) data associated with the reservoir.

2. The system of claim 1, wherein the data outputs comprise a notification of a user configurable alert associated with a presence of a specific level of a chemical.

3. The system of claim 1, wherein the knowledge engine comprises:
    at least one inference engine;
    an alert engine;
    a remedy prescription engine;
    a common database; and
    a visual analytic display engine.

4. The system of claim 3, wherein the knowledge engine and user data interface are remotely located from the reservoir associated with the field inputs, wherein the field inputs are transmitted from the reservoir to the remote knowledge engine via a communications network.

5. The system of claim 4, wherein the chemical sensing data is further supplied by at least one chemical sensor disposed in a flow of fluids, liquids or gasses, from the reservoir.

6. The system of claim 5, wherein the knowledge engine comprises at least one processing device, and the plurality of field inputs comprises data stored in a memory for use by the at least one processing device.

7. The system of claim 6, further comprising:
    at least one wellhead fluid analyzer comprising a housing inserted into the well flow and a sensing apparatus within the housing; and
    a connection to a data exfiltration system.

8. The system of claim 7, wherein a plurality of wells are located in the reservoir, and the at least one wellhead fluid analyzer comprises a plurality of wellhead fluid analyzers, each wellhead fluid analyzer installed at one of the wells, wherein each wellhead fluid analyzer includes a connection to the data exfiltration system.

9. The system of claim 8, further comprising a local area network of wireless devices, each wireless device communicatively coupled to one of the wellhead fluid analyzers.

10. The system of claim 3, wherein the alert engine is rule based.

11. The system of claim 4, wherein the knowledge engine is configured to produce prescriptive remedies for individual well problems or reservoir problems.

12. The system of claim 5, wherein the at least one chemical sensor disposed in the flow of fluids, liquids or gasses comprises a plurality of chemical sensors disposed in reservoir fluids below the earth's surface.

13. The system of claim 12, further comprising:
    a local area network of wireless devices, the local area network comprising:
        a wireless communication transceiver attached to each of one or more sensing apparatuses; and a wellhead communication transceiver installed at the wellhead; and a connection to a data exfiltration system attached to the wellhead communication transceiver.

14. The system of claim 13, wherein the wireless communication transceiver attached to each sensing apparatus and the wellhead communication transceiver are dual frequency devices configured to operate in acoustic and ultrasonic bands.

15. The system of claim 5, wherein the field inputs are taken from a plurality of wells.

16. The system of claim 15, wherein the data outputs include contour mapping of subterranean chemical pools.

17. The system of claim 15, wherein the data outputs include chemical flows between wells.

18. A method for well and reservoir management for optimized production of fluids in a reservoir, the method comprising:

receiving, at a knowledge engine, a plurality of field inputs;

processing and analyzing, at the knowledge engine, the field inputs;

providing, at the knowledge engine, a plurality of data outputs for presentation to an operator; and displaying, at a user data interface, the plurality of data outputs, wherein the plurality of field inputs comprises (i) dynamic, continuously measured chemical sensing data supplied by at least one chemical sensor installed into surface equipment at a wellhead at a well, (ii) at least one of: temperature, pressure, flow rate and concentration of production components from one or more individual wells located within the reservoir, and (iii) at least one of: seismic surveys of the reservoir, permeability, geochemistry and lithology of rock formations, and geographic information system (GIS) data associated with the reservoir.

19. The method of claim 18, wherein the knowledge engine and user data interface are remotely located from the reservoir associated with the field inputs, wherein the field inputs are transmitted from the reservoir to the remote knowledge engine via a communications network.

20. The method of claim 18, wherein the knowledge engine comprises at least one processing device, and the plurality of field inputs comprises data stored in a memory for use by the at least one processing device.

21. The method of claim 18, wherein the chemical sensing data is further supplied by at least one chemical sensor installed below the earth's surface at a well in the reservoir, the at least one chemical sensor disposed in a flow of fluids or gasses in the well.

22. The method of claim 18, wherein the field inputs are taken from a plurality of wells.

* * * * *